(12) United States Patent
Matsunaga et al.

(10) Patent No.: US 11,298,419 B2
(45) Date of Patent: Apr. 12, 2022

(54) QUAIL EGG ALLERGY ANTIGEN

(71) Applicant: HOYU CO., LTD., Aichi (JP)

(72) Inventors: Kayoko Matsunaga, Aichi (JP); Akiko Yagami, Aichi (JP); Yasuto Kondo, Aichi (JP); Kazuhiro Hara, Aichi (JP); Masashi Nakamura, Aichi (JP); Yuji Aoki, Aichi (JP)

(73) Assignee: HOYU CO., LTD., Aichi (JP)

( * ) Notice: Subject to any disclaimer, the term of this patent is extended or adjusted under 35 U.S.C. 154(b) by 0 days.

(21) Appl. No.: 15/576,080

(22) PCT Filed: May 25, 2016

(86) PCT No.: PCT/JP2016/065522
§ 371 (c)(1),
(2) Date: Nov. 21, 2017

(87) PCT Pub. No.: WO2016/190376
PCT Pub. Date: Dec. 1, 2016

(65) Prior Publication Data
US 2018/0193449 A1 Jul. 12, 2018

(30) Foreign Application Priority Data

May 25, 2015 (JP) .............................. JP2015-105856

(51) Int. Cl.
| A61K 39/35 | (2006.01) |
| C07K 14/465 | (2006.01) |
| G01N 33/53 | (2006.01) |
| A23L 15/00 | (2016.01) |
| C07K 16/18 | (2006.01) |

(52) U.S. Cl.
CPC .............. *A61K 39/35* (2013.01); *A23L 15/00* (2016.08); *C07K 14/465* (2013.01); *C07K 16/18* (2013.01); *G01N 33/53* (2013.01); *A23V 2002/00* (2013.01); *G01N 2333/465* (2013.01)

(58) Field of Classification Search
None
See application file for complete search history.

(56) References Cited

U.S. PATENT DOCUMENTS

| 6,420,337 B1 * | 7/2002 | Iyer ........................ C07K 14/46 424/450 |
| 8,753,698 B2 * | 6/2014 | Van Amerongen ..... A61P 43/00 426/63 |
| 2007/0275037 A1 * | 11/2007 | Ding ........................ C12N 15/81 424/442 |
| 2009/0029005 A1 * | 1/2009 | Van Amerongen .... A61K 35/54 426/63 |

FOREIGN PATENT DOCUMENTS

| EP | 1440978 A1 | 7/2004 |
| JP | 2002-286716 A | 10/2002 |
| JP | 2006115761 A | 5/2006 |
| JP | 2008-137968 A | 6/2008 |
| JP | 2011-033544 A | 2/2011 |
| JP | 2011-033546 A | 2/2011 |
| JP | 2011-033547 A | 2/2011 |
| JP | 2011-033548 A | 2/2011 |
| JP | 4919486 B2 | 4/2012 |
| JP | 5894695 B1 | 3/2016 |
| KR | 20100040166 A | 4/2010 |
| WO | WO 2001/07472 * | 2/2001 ............. C07K 14/46 |
| WO | 2005040400 A2 | 5/2005 |
| WO | 2006/009448 A1 | 1/2006 |
| WO | WO-2011122127 A1 * | 10/2011 ......... C07K 5/06026 |

OTHER PUBLICATIONS

Van het Schip et al. Nucleotide sequence of a chicken vitellogenin gene and derived amino acid sequence of the encoded yolk precursor protein. JMB 196(2):245-260, 1987.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Kinnunen et al. 'Potential of an altered peptide ligand of lipocalin allergen Bos d 2 for peptide immunotherapy.' J. Allerg. Clin. Immunol.' 119:965-72, 2007.*
Schein et al. 'Bioinformatics approaches to classifying allergens and predicting cross-reactivity.' Immunol. Allergy Clin. North Am. 27(1):1 -27, 2007.*
Friedl-Hajek et al. 'Identification of a highly promiscuous and an HLA allele-specific T-cell epitope in the birch major allergen Bet v 1 :HLA restriction, epitope mapping and TCR sequence comparisons.' Clin. Exp. Allergy 29:478-487, 1999.*
Amo et al. 'Gal d 6 Is the Second Allergen Characterized from Egg Yolk.' J. Agric. Food Chem. 58:7453-7457, 2010.*
Yamamura et al. 'Precursor-product relationship between chicken vitellogenin and the yolk proteins the 40 kDa yolk plasma glycoprotein is derived from the C-terminal cysteine-rich domain of vitellogenin II.' Biochimica et Biophysica Acta 1244 (1995) 384-394.*
Hara et al., "Antigen Analysis of Young Child Case Who Can Ingest Chicken Egg But Repeats Vomiting and Diarrhea Upon Ingestion of Quail Egg", Allergy vol. 64 No. 34 p. 606, Apr. 25, 2015.
International Search Report for PCT/JP2016/065522 dated Jul. 19, 2016. p. 1-1.
European search report for EP Application 16800080.0 dated May 29, 2018, p. 1-4.
Takahashi et al., Immunochemical characterization of ovomucoid from Japanese quail egg white using monoclonal antibodies. J Nutr Sci Vitaminol (Tokyo). Aug. 1999;45(4):491-500.

* cited by examiner

*Primary Examiner* — Nora M Rooney
(74) *Attorney, Agent, or Firm* — McCarter & English, LLP; Yu Lu

(57) ABSTRACT

The present invention provides novel antigens of an allergy to a quail egg, methods and kits for diagnosing an allergy to a quail egg, pharmaceutical compositions comprising such an antigen, and quail eggs or processed products of quail egg which are devoid of such an antigen.

6 Claims, 3 Drawing Sheets

Specification includes a Sequence Listing.

QUAIL EGG ALLERGY ANTIGEN

CROSS-REFERENCE TO RELATED APPLICATIONS

This application is a 35 U.S.C. § 371 national stage filing of International Application No. PCT/JP2016/065522, filed on May 25, 2016, which in turn claims priority to Japanese Patent Application No. 2015-105856, filed on May 25, 2015, the entire contents of which are incorporated herein by reference.

REFERENCE TO SEQUENCE LISTING

This application contains a Sequence Listing in computer readable form, which has been submitted electronically via EFS-web in ASCII format. Said ASCII copy, created on Mar. 12, 2021, is named 129149-00102_SL.txt and is 21,859 bytes in size. The computer readable form of the sequence listing is part of the specification or is otherwise incorporated herein by reference.

TECHNICAL FIELD

The present invention relates to novel antigens of an allergy to a quail egg. This invention also relates to kits, compositions and methods for diagnosing an allergy to a quail egg. This invention further relates to pharmaceutical compositions comprising such an antigen, quail eggs or processed products of quail egg which are devoid of such an antigen, and testers for determining the presence or absence of such an antigen.

BACKGROUND ART

In serum and tissues of allergic patients, IgE antibodies specific to particular antigens are produced. Physiological consequences caused by interaction between such IgE antibodies and such particular antigens elicit allergic reactions. In the process of production of conventional allergy testing agents, antigen reagents are commonly prepared simply by grinding a candidate allergenic food, material or the like (Patent Literature 1). As seen above, conventional antigen reagents do not necessarily contain only a particular antigenic protein inducing an allergic reaction (allergen component), and rather contain different types of protein components. Thus, conventional antigen reagents contain varied amounts of allergen components. For this reason, the only case where conventional allergy tests have permitted detection of a positive allergic reaction is when in a conventional antigen reagent containing many types of proteins, a particular protein acting as an allergen component is present in an amount exceeding a threshold that allows determination of a positive reaction for binding to an IgE antibody. However, no determination of a positive reaction was possible when using a conventional allergy testing agent in patients possessing an IgE antibody binding to an allergen component present in small amounts in an allergen such as food.

The severity and symptoms of an allergic reaction do not necessarily correlate with the content of an allergen component. Even when a patient's IgE antibody reacts with an allergen component present in trace amounts in a candidate allergic food, material or the like, the allergic reaction may develop allergic symptoms or may affect the severity of those symptoms.

Therefore, in order to enhance the reliability of allergy tests, it is necessary to exhaustively identify allergen components in candidate allergic foods and materials.

Meanwhile, in the field of protein separation and purification, various efforts have conventionally been made to develop methods for separating and purifying a protein or nucleic acid of interest from cell extracts or the like. Such methods may well be exemplified by dialysis based on salt concentration, and centrifugal separation.

Other efforts have been made to develop many purification methods based on electric charges of proteins or nucleic acid residues or on the difference in molecular weight. Electric charge-based purification methods can be exemplified by column chromatography using ion exchange resins, and isoelectric focusing. Purifications based on molecular weight difference can be exemplified by centrifugal separation, molecular-sieve column chromatography, and SDS-PAGE (sodium dodecyl sulfate-polyacrylamide gel electrophoresis).

In recent years, a method for separating and purifying many different proteins from a small amount of sample has been used, which is more specifically a two-dimensional electrophoresis consisting of isoelectric focusing in the first dimension, followed by SDS-PAGE in the second dimension. The present applicant has conventionally developed some 2D electrophoresis methods with high separation ability (Patent Literatures 2-5).

CITATION LIST

Patent Literatures

PTL 1: Japanese Patent Application Publication No. JP 2002-286716
PTL 2: Japanese Patent Application Publication No. JP 2011-33544
PTL 3: Japanese Patent Application Publication No. JP 2011-33546
PTL 4: Japanese Patent Application Publication No. JP 2011-33547
PTL 5: Japanese Patent Application Publication No. JP 2011-33548

SUMMARY OF INVENTION

Technical Problem

The present invention provides novel antigens of an allergy to a quail egg. This invention also provides methods and kits for diagnosing an allergy to a quail egg. This invention further provides pharmaceutical compositions comprising such an antigen, quail eggs or processed products of quail egg which are devoid of such an antigen, and testers for determining the presence or absence of such an antigen.

Solution to Problem

In order to solve the aforementioned problems, the present inventors had made intensive studies to identify causative antigens of an allergy to a quail egg. As a result, the inventors succeeded in identifying antigens to which an IgE antibody in the serum of a quail egg-allergic patient specifically binds. The present invention has been completed based on this finding.

Thus, in one embodiment, the present invention can be as defined below.

[1] A kit for diagnosing an allergy to a quail egg, the kit comprising, as an antigen, at least one protein defined below in (1) or (2):
(1) (1A) vitellogenin-1 protein or a variant thereof, which is a protein defined below in any of (1A-a) to (1A-e):
(1A-a) a protein comprising an amino acid sequence with deletion, substitution, insertion or addition of one or several amino acids in SEQ ID NO:18;
(1A-b) a protein comprising an amino acid sequence having at least 70% identity to the amino acid sequence of SEQ ID NO:18;
(1A-c) a protein comprising an amino acid sequence encoded by a nucleotide sequence with deletion, substitution, insertion or addition of one or several nucleotides in SEQ ID NO:17;
(1A-d) a protein comprising an amino acid sequence encoded by a nucleotide sequence having at least 70% identity to the nucleotide sequence of SEQ ID NO:17; or
(1A-e) a protein comprising an amino acid sequence encoded by a nucleic acid that hybridizes under stringent conditions with a nucleic acid having a nucleotide sequence complementary to the nucleotide sequence of SEQ ID NO:17; or
(1B) a protein comprising at least one amino acid sequence selected from the group consisting of SEQ ID NOs:1-4, 6-16 and 18;
(2) (2A) vitellogenin-2 protein or a variant thereof, which is a protein defined below in any of (2A-a) to (2A-e):
(2A-a) a protein comprising an amino acid sequence with deletion, substitution, insertion or addition of one or several amino acids in SEQ ID NO:24;
(2A-b) a protein comprising an amino acid sequence having at least 70% identity to the amino acid sequence of SEQ ID NO:24;
(2A-c) a protein comprising an amino acid sequence encoded by a nucleotide sequence with deletion, substitution, insertion or addition of one or several nucleotides in SEQ ID NO:23;
(2A-d) a protein comprising an amino acid sequence encoded by a nucleotide sequence having at least 70% identity to the nucleotide sequence of SEQ ID NO:23; or
(2A-e) a protein comprising an amino acid sequence encoded by a nucleic acid that hybridizes under stringent conditions with a nucleic acid having a nucleotide sequence complementary to the nucleotide sequence of SEQ ID NO:23; or
(2B) a protein comprising at least one amino acid sequence selected from the group consisting of SEQ ID NOs:19-22 and 24.
[2] A composition for diagnosing an allergy to a quail egg, the composition comprising, as an antigen, at least one of protein as defined above in (1) or (2) of [1].
[3] A method for providing an indicator for diagnosing an allergy to a quail egg in a subject, the method comprising the steps of:
(i) contacting a sample obtained from the subject with an antigen, wherein the sample is a solution comprising an Ig antibody;
(ii) detecting binding between the IgE antibody present in the sample from the subject and the antigen; and
(iii) when the binding between the IgE antibody in the subject and the antigen is detected, an indicator of the fact that the subject is allergic to a quail egg is provided; wherein the antigen is at least one of protein as defined above in (1) or (2) of [1].

[4] A pharmaceutical composition comprising at least one of protein (1) or protein (2) as defined above in [1].
[5] The pharmaceutical composition as set forth in [4], wherein the pharmaceutical composition is intended for the treatment of an allergy to a quail egg.
[6] A quail egg or a processed product of quail egg in which an antigen is eliminated or reduced, wherein the antigen is at least one of protein as defined above in (1) or (2) of [1].
[7] A tester for determining the presence or absence of a causative antigen of a quail egg allergy in an object of interest, the tester comprising an antibody that binds to at least one of protein as defined above in (1) or (2) of [1].
[8] A tester for determining the presence or absence of a causative antigen of a quail egg allergy in an object of interest, the tester comprising a primer having a nucleotide sequence complementary to at least one of the nucleotide sequence of SEQ ID NO:17 or the nucleotide sequence of SEQ ID NO:23.
[9] A quail-derived antigen, which is a protein as defined above in (1) or (2) of [1] and is causative of an allergy to a quail egg.

Advantageous Effects of Invention

The present invention can provide novel antigens of an allergy to a quail egg. Since the antigens (allergen components) that trigger a quail egg allergy were identified according to this invention, this invention can provide highly sensitive methods and kits for diagnosing an allergy to a quail egg, pharmaceutical compositions comprising such an antigen, quail eggs or processed products of quail egg which are devoid of such an antigen, and testers for determining the presence or absence of such an antigen.

DESCRIPTION OF EMBODIMENTS

Figure 1:
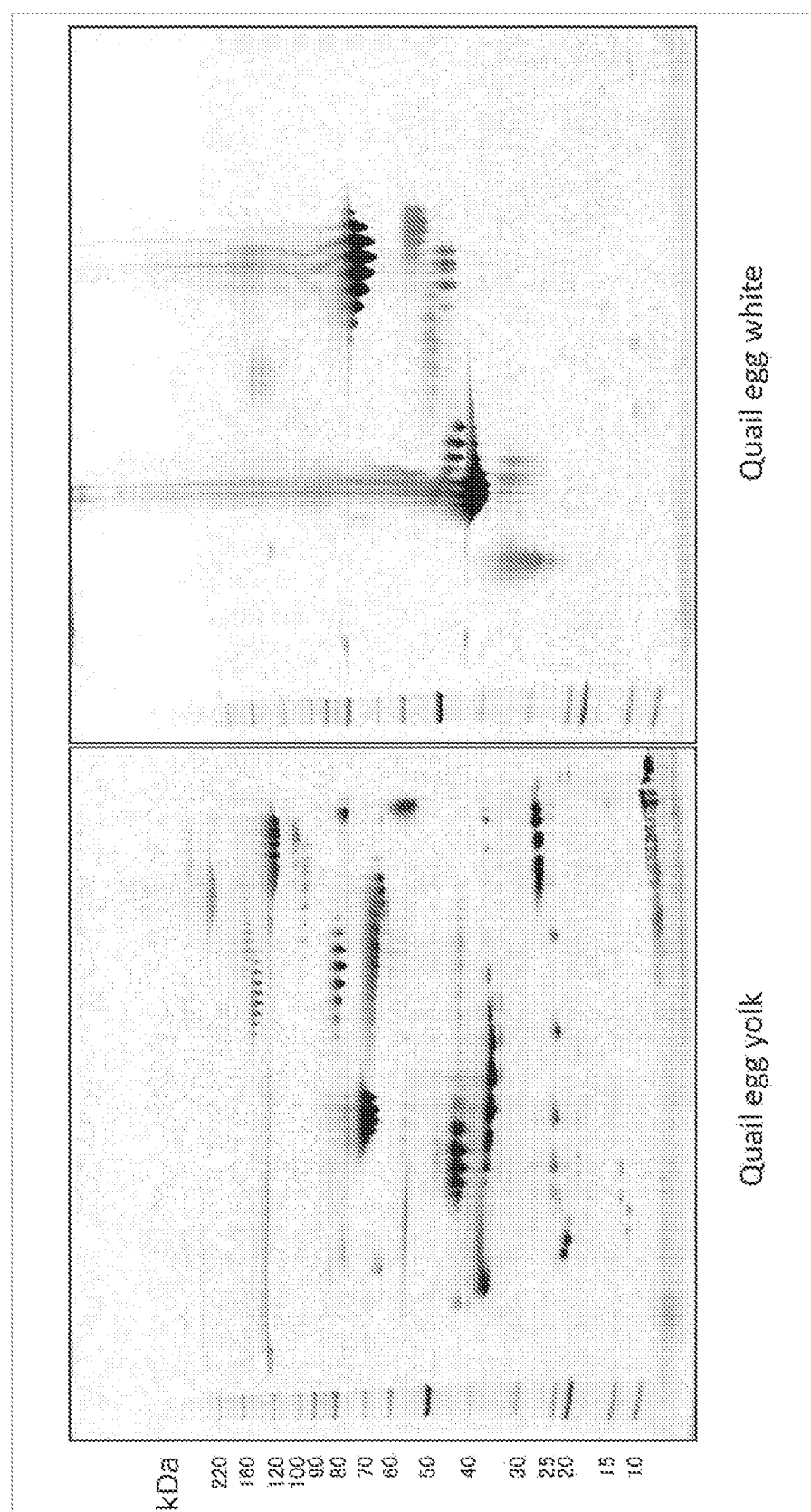
FIG. 1 is a set of photos of gels showing two-dimensional electrophoresis patterns of proteins present in quail egg yolk and white. The left photo shows a 2D electrophoresis pattern of quail egg yolk proteins, and the right photo shows a 2D electrophoresis pattern of quail egg white proteins. The band at the left of each of the photos is a molecular weight marker band.

Hereunder, the present invention will be specifically described, but this invention is not limited by the specific descriptions provided below.

Unless otherwise defined herein, all scientific and technical terms used in relation to the present invention shall have meanings commonly understood by those skilled in the art.

As referred to herein, the "allergy" refers to the state in which, when a certain antigen enters the body of a living individual sensitized to said antigen, the living individual shows a hypersensitive reaction detrimental to him/her. In blood and serum of individuals with many food-allergic diseases, IgE antibodies specific to antigens are produced. IgE antibodies bind to mast cells or basophils. When an antigen specific to such an IgE antibody enters again the body of a patient with an allergic disease, said antigen combines with the IgE antibody bound to mast cells or basophils, and the IgE antibody crosslinks said antigen on the cell surface, resulting in physiological effects of IgE antibody-antigen interaction. Examples of such physiological effects include release of histamine, serotonin, heparin, eosinophil chemotactic factors, leucotrienes, or the like. These released substances provoke an allergic reaction resulting from the combination of an IgE antibody with particular antigens. Such allergic reactions caused by particular antigens occur through the aforementioned pathway.

As referred to herein, the "allergy to a quail egg" refers to the state in which an individual has an allergic reaction caused by proteins, etc. present in a quail egg which act as an antigen. The allergy to a quail egg can produce an allergic reaction upon contact with, or consumption of, an antigen present in quail egg. In general, allergic reactions caused by consumption of foods are particularly referred to as "food allergies". The allergy to a quail egg may be a food allergy.

As referred to herein, the "antigen" refers to a substance that provokes an allergic reaction, and is also referred to as an "allergen component". The antigen is preferably a protein.

As referred to herein, the "protein" refers to a molecule having a structure in which naturally occurring amino acids are joined together by peptide bond. The number of amino acids present in a protein is not particularly limited, but proteins having about 2 to 50 amino acids joined together by peptide bond are in some cases called "peptides". In the case where amino acids can form different enantiomers, the amino acids are understood to form an L-enantiomer, unless otherwise indicated. In the present specification, the amino acid sequences of proteins or peptides are represented by one-letter symbols of amino acids in accordance with standard usage and the notational convention commonly used in the art. The leftward direction represents the amino-terminal direction, and the rightward direction represents the carboxy-terminal direction.

Identification of Antigens

Proteins present in a quail egg were analyzed by the aforementioned technique to identify causative antigens of an allergy to a quail egg. To be specific, proteins of a quail egg yolk were subjected to two-dimensional electrophoresis under the conditions described below.

The electrophoresis in the first dimension was isoelectric focusing, which was performed using isoelectric focusing gels with a gel-strip length of 5 to 10 cm and a gel pH range of 3 to 10. The pH gradient of the gels in the direction of electrophoresis was as follows: with the total gel-strip length being taken as 1, the gel-strip length up to pH 5 was "a=0.15 to 0.3", the gel-strip length from pH 5 to 7 was "b=0.4 to 0.7", and the gel-strip length above pH 7 was "c=0.15 to 0.3". More specifically, the isoelectric focusing was performed using the IPG gels, Immobiline Drystrip (pH3-10NL), produced by GE Healthcare Bio-Sciences Corporation (hereinafter abbreviated as "GE"). The electrophoresis system used was IPGphor produced by GE. The maximum current of the electrophoresis system was limited to 75 µA per gel strip. The voltage program adopted to perform the first-dimensional isoelectric focusing was as follows: (1) a constant voltage step was performed at a constant voltage of 300 V until the volt-hours reached 750 Vhr (the current variation width during electrophoresis for 30 minutes before the end of this step was 5 µA); (2) the voltage was increased gradually to 1000 V for 300 Vhr; (3) the voltage was further increased gradually to 5000 V for 4500 Vhr; and then (4) the voltage was held at a constant voltage of 5000 V until the total Vhr reached 12000.

The electrophoresis in the second dimension was SDS-PAGE, which was performed using polyacrylamide gels whose gel concentration at the distal end in the direction of electrophoresis was set to 3 to 6% and whose gel concentration at the proximal end was set to a higher value than that at the distal end. More specifically, the SDS-PAGE was performed using NuPAGE 4-12% Bris-Tris Gels (IPG well, Mini, 1 mm) produced by Life Technologies. The electrophoresis system used was XCell SureLock Mini-Cell produced by Life Technologies. The electrophoresis was run at a constant voltage of 200 V for about 45 minutes using an electrophoresis buffer composed of 50 mM MOPS, 50 mM Tris base, 0.1% (w/v) SDS and 1 mM EDTA.

As a result of the two-dimensional electrophoresis performed on proteins of a quail egg yolk under the aforementioned conditions, the following two protein spots appeared on the gels used: one protein spot with an isoelectric point of 5 to 9 and a molecular weight of around 45 kDa (hereinafter, the proteins in this spot are referred to as "antigens in spot 1"), and the other protein spot with an isoelectric point of 7 to 12 and a MW of around 35 kDa (hereinafter, the proteins in this spot are referred to as "antigens in spot 2"). The proteins in these spots were found to specifically bind to an IgE antibody of a quail egg-allergic patient.

Antigens

Antigens in Spot 1

As the result of sequence identification of the antigens in spot 1 by mass spectroscopy, the following amino acid sequences were detected.

```
                              (SEQ ID NO: 1)
SFKPVYTDVPIEK (SEQ ID NO: 2)
TFAVTRNIEDLAASK (SEQ ID NO: 3)
MTPVLLPEAVPDIMK (SEQ ID NO: 4)
KSVHAAFIK
```

-continued

```
                                           (SEQ ID NO: 6)
PVYTDVPIEK (SEQ ID NO: 7)
IQVTIQAGDQAPTKM (SEQ ID NO: 8)
ALPHDKPFASGYLK (SEQ ID NO: 9)
DWETNYDFK (SEQ ID NO: 10)
EETNVITVSSK (SEQ ID NO: 11)
IQVTIQAGDQAPTK (SEQ ID NO: 12)
NTIQNVLQAWYGPDEK (SEQ ID NO: 13)
RLISSLQSGIGRQLTK (SEQ ID NO: 14)
SVHAAFIK (SEQ ID NO: 15)
TFAVTRNIEDLAA (SEQ ID NO: 16)
VNAHVPVNVVATIQMK
```

Also, the mass spectroscopic data obtained for spot 1 on a mass spectrometer (MS data for SEQ ID NOs:1-4 and 6-16) were analyzed by comparing them against the NCBI protein data, and as a result, the antigens in question were identified as different portions of vitellogenin-1 protein (SEQ ID NO:18) derived from Japanese quail (*Coturnix japonica*). SEQ ID NO:1 corresponds to amino acids 329 to 341 of SEQ ID NO:18; SEQ ID NO:2 corresponds to amino acids 213 to 228 of SEQ ID NO:18; SEQ ID NO:3 corresponds to amino acids 229 to 243 of SEQ ID NO:18; SEQ ID NO:4 corresponds to amino acids 305 to 313 of SEQ ID NO:18; SEQ ID NO:6 corresponds to amino acids 332 to 341 of SEQ ID NO:18; SEQ ID NO:7 corresponds to amino acids 342 to 356 of SEQ ID NO:18; SEQ ID NO:8 corresponds to amino acids 20 to 33 of SEQ ID NO:18; SEQ ID NO:9 corresponds to amino acids 1 to 9 of SEQ ID NO:18; SEQ ID NO:10 corresponds to amino acids 203 to 213 of SEQ ID NO:18; SEQ ID NO:11 corresponds to amino acids 342 to 355 of SEQ ID NO:18; SEQ ID NO:12 corresponds to amino acids 47 to 62 of SEQ ID NO:18; SEQ ID NO:13 corresponds to amino acids 68 to 83 of SEQ ID NO:18; SEQ ID NO:14 corresponds to amino acids 306 to 313 of SEQ ID NO:18; SEQ ID NO:15 corresponds to amino acids 214 to 226 of SEQ ID NO:18; and SEQ ID NO:16 corresponds to amino acids 175 to 190 of SEQ ID NO:18.

Accordingly, in the present invention, the antigen in spot 1 can be any of (1A-a) to (1A-e) and (1B) as defined below:
(1A-a) a protein comprising an amino acid sequence with deletion, substitution, insertion or addition of one or several amino acids in SEQ ID NO:18;
(1A-b) a protein comprising an amino acid sequence having an identity of at least 70%, preferably at least 75%, at least 80%, at least 85%, at least 90%, at least 95%, at least 97%, at least 98%, or at least 99%, to the amino acid sequence of SEQ ID NO:18;
(1A-c) a protein comprising an amino acid sequence encoded by a nucleotide sequence with deletion, substitution, insertion or addition of one or several nucleotides in SEQ ID NO:17;
(1A-d) a protein comprising an amino acid sequence encoded by a nucleotide sequence having an identity of at least 70%, preferably at least 75%, at least 80%, at least 85%, at least 90%, at least 95%, at least 97%, at least 98%, or at least 99%, to the nucleotide sequence of SEQ ID NO:17;
(1A-e) a protein comprising an amino acid sequence encoded by a nucleic acid that hybridizes under stringent conditions with a nucleic acid having a nucleotide sequence complementary to the nucleotide sequence of SEQ ID NO:17;
(1B) a protein comprising at least one amino acid sequence selected from the group consisting of SEQ ID NOs:1-4, 6-16 and 18, preferably a protein comprising at least 2, 3, 4, 5, 6, 7, 8, 9, 10, 11, 12, 13, 14, 15, 16 or all of the amino acid sequences of SEQ ID NOs:1-4, 6-16 and 18, more preferably a protein comprising at least one amino acid sequence selected from the group consisting of SEQ ID NOs:1, 2, 6, 8 to 16 and 18, still more preferably a protein comprising at least 2, 3, 4, 5, 6, 7, 8, 9, 10, 11, 12 or all of the amino acid sequences of SEQ ID NOs:1, 2, 6, 8 to 16 and 18. As referred to above, the amino acid sequence of any of SEQ ID NOs:1-4, 6-16 and 18 may be an amino acid sequence derived therefrom by deletion, substitution, insertion or addition of one or several amino acids.

The proteins of (1A-a) to (1A-e) and (1B) as defined above also include those proteins whose amino acid residues are modified by phosphorylation, sugar chain modification, aminoacylation, ring-opening, deamination or the like.

The proteins of (1A-a) to (1A-e) and (1B) as defined above can be proteins that are found in a protein spot with a molecular weight of around 35 to 50 kDa, preferably around 40 to 47 kDa, more preferably around 42 to 47 kDa, on gels used in the two-dimensional electrophoresis performed under the conditions described above in the subsection titled "Identification of antigens". The proteins of (1A-a) to (1A-e) and (1B) can also be proteins that are found in a protein spot with an isoelectric point of 5 to 9, preferably 6 to 8, on gels used in the 2D electrophoresis performed under the aforementioned conditions. Alternatively, the proteins of (1A-a) to (1A-e) and (1B) can be proteins that are found in a protein spot with a molecular weight of around 35 to 50 kDa, preferably around 40 to 47 kDa, more preferably around 42 to 47 kDa, and an isoelectric point of 5 to 9, preferably 6 to 8, on gels used in the 2D electrophoresis performed under the aforementioned conditions.

Preferably, the proteins of (1A-a) to (1A-e) and (1B) as defined above are causative of an allergy to a quail egg.

Antigens in Spot 2

As the result of sequence identification of the antigens in spot 2 by mass spectroscopy, the following amino acid sequences were detected.

```
                                           (SEQ ID NO: 19)
LCADASVLNAHK (SEQ ID NO: 20)
TVQLAGVDSK (SEQ ID NO: 21)
AEAPSAVLNNLK (SEQ ID NO: 22)
GGLQLVVFADTDSVK
```

Also, the mass spectroscopic data obtained for spot 2 on a mass spectrometer (MS data for SEQ ID NOs:19 to 22) were analyzed by comparing them against the NCBI protein data, and as a result, the antigens in question were identified as different portions of vitellogenin-2 protein (SEQ ID NO:24) from Japanese quail (*Coturnix japonica*). SEQ ID NO:19 corresponds to amino acids 50 to 61 of SEQ ID NO:24; SEQ ID NO:20 corresponds to amino acids 395 to 404 of SEQ ID NO:24; SEQ ID NO:21 corresponds to amino acids 191 to 202 of SEQ ID NO:24; and SEQ ID NO:22 corresponds to amino acids 18 to 32 of SEQ ID NO:24.

Accordingly, the antigens in spot 2 can be as defined below in (2A-a) to (2A-e) and (2B):

(2A-a) a protein comprising an amino acid sequence with deletion, substitution, insertion or addition of one or several amino acids in SEQ ID NO:24;

(2A-b) a protein comprising an amino acid sequence having an identity of at least 70%, preferably at least 75%, at least 80%, at least 85%, at least 90%, at least 95%, at least 97%, at least 98%, or at least 99%, to the amino acid sequence of SEQ ID NO:24;

(2A-c) a protein comprising an amino acid sequence encoded by a nucleotide sequence with deletion, substitution, insertion or addition of one or several nucleotides in SEQ ID NO:23;

(2A-d) a protein comprising an amino acid sequence encoded by a nucleotide sequence having an identity of at least 70%, preferably at least 75%, at least 80%, at least 85%, at least 90%, at least 95%, at least 97%, at least 98%, or at least 99%, to the nucleotide sequence of SEQ ID NO:23;

(2A-e) a protein comprising an amino acid sequence encoded by a nucleic acid that hybridizes under stringent conditions with a nucleic acid having a nucleotide sequence complementary to the nucleotide sequence of SEQ ID NO:23;

(2B) a protein comprising at least one amino acid sequence selected from the group consisting of SEQ ID NOs:19-22 and 24, preferably a protein comprising at least 2, 3, 4 or all of the amino acid sequences of SEQ ID NOs:19-22 and 24, more preferably a protein comprising the amino acid sequence(s) of SEQ ID NO(s):21, 22 and/or 24. As referred to above, the amino acid sequence of any of SEQ ID NOs:19-22 and 24 may be an amino acid sequence derived therefrom by deletion, substitution, insertion or addition of one or several amino acids.

The proteins of (2A-a) to (2A-e) and (2B) as defined above also include those proteins whose amino acid residues are modified by phosphorylation, sugar chain modification, aminoacylation, ring-opening, deamination or the like.

The proteins of (2A-a) to (2A-e) and (2B) as defined above can be proteins that are found in a protein spot with a molecular weight of around 30 to 50 kDa, preferably around 30 to 40 kDa, more preferably around 32 to 37 kDa, on gels used in the two-dimensional electrophoresis performed under the conditions described above in the subsection titled "Identification of antigens". The proteins of (2A-a) to (2A-e) and (2B) can also be proteins that are found in a protein spot with an isoelectric point of 7 to 12, preferably 8 to 10, on gels used in the 2D electrophoresis performed under the aforementioned conditions. Alternatively, the proteins of (2A-a) to (2A-e) and (2B) can be proteins that are found in a protein spot with a molecular weight of around 30 to 50 kDa, preferably around 30 to 40 kDa, more preferably around 32 to 37 kDa, and an isoelectric point of 7 to 12, preferably 8 to 10, on gels used in the 2D electrophoresis performed under the aforementioned conditions.

Preferably, the proteins of (2A-a) to (2A-e) and (2B) as defined above are causative of an allergy to a quail egg.

By stating herein "deletion, substitution, insertion or addition of one or several amino acids" in relation to amino acid sequence, it is meant that in an amino acid sequence of interest, one or several amino acids (e.g., 40%, preferably 30%, 20%, 10% or 5%, of amino acids with respect to the total length of the amino acid sequence) are deleted, one or several amino acids are substituted by any other amino acids, any other amino acids are inserted, and/or any other amino acids are added.

Among the aforementioned modifications, substitution is preferably conservative substitution. The "conservative substitution" refers to the substitution of a certain amino acid residue by a different amino acid residue having similar physicochemical characteristics, and can be any type of substitution as long as it does not substantially change the characteristics of the structure of the original sequence—for example, any type of substitution is acceptable as long as any substituted amino acids do not disrupt the helical structure of the original sequence or other secondary structures that characterize the original sequence. The following gives examples of separate groups of amino acid residues that are conservatively substitutable with each other, but substitutable amino acid residues are not limited to the examples given below.

Group A: leucine, isoleucine, valine, alanine, methionine
Group B: asparatic acid, glutamic acid
Group C: asparagine, glutamine
Group D: lysine, arginine
Group E: serine, threonine
Group F: phenylalanine, tyrosine In the case of non-conservative substitution, one member belonging to one of the aforementioned groups can be replaced with a member belong to any other group. For example, in order to eliminate the possibility of unwanted sugar-chain modification, amino acid residues of group B, D or E as listed above may be substituted by those of any other group. Also, cysteine residues may be deleted or substituted by any other amino acid residues to prevent them from being folded into a protein in its tertiary structure. Also, in order to maintain the balance between hydrophilicity and hydrophobicity or to increase hydrophilicity for the purpose of facilitating synthesis, any amino acid residues may be substituted in consideration of the hydropathy scales of amino acids, which are a measure of the hydrophilic and hydrophobic properties of amino acids (J. Kyte and R. Doolittle, *J. Mol. Biol.*, Vol. 157, p. 105-132, 1982).

As referred to herein, the percent identity between two amino acid sequences can be determined by visual inspection and mathematical calculation. Alternatively, the percent identity can be determined using a computer program. Examples of such computer programs include, but are not limited to, BLAST (Altschul, et al., *J. Mol. Biol.,* 215: 403-410 (1990)), and ClustalW. In particular, various conditions (parameters) for sequence identity searches with the BLAST program are described in Altschul, et al. (*Nucl. Acids. Res.,* 25, p. 3389-3402, 1997), and are publicly available on the websites of the National Center for Biotechnology Information (NCBI) and DNA Data Bank of Japan (DDBJ) (Altschul, et al., *BLAST Handbook*, NCB/NLM/NIH Bethesda, Md. 20894). Also, the percent identity can be determined using a genetic information processing software program, such as GENETYX Ver.7 (Genetyx Corporation), DINASIS Pro (Hitachi Software Engineering Co., Ltd.), or Vector NTI (Infomax Inc.).

By stating herein "deletion, substitution, insertion or addition of one or several nucleotides" in relation to nucleotide sequence, it is meant that in a nucleotide sequence of interest, one or several nucleotides (e.g., 30%, preferably 25%, 20%, 15%, 10%, 5%, 3%, 2% or 1%, of nucleotides with respect to the total length of the nucleotide sequence) are deleted, one or several nucleotides are substituted by any other nucleotides, any other nucleotides are inserted, and/or any other nucleotides are added. It is preferable that such a nucleotide deletion, substitution, insertion or addition should not give rise to a frame shift in an amino acid coding sequence.

As referred to herein, the percent identity between two nucleotide sequences can be determined by visual inspection and mathematical calculation. Alternatively, the percent identity can be determined using a computer program. Alternatively, the percent identity can be determined using a computer program. Examples of such sequence comparison computer programs include, but are not limited to, the BLASTN program, version 2.2.7, available on the website of the National Library of Medicine (http://www.ncbi.nlm.nih.gov/blast/bl2seq/bls.html) (Altschul, et al. (1990) J. Mol. Biol., 215: 403-10), or the WU-BLAST 2.0 algorithm. Standard default parameter settings for WU-BLAST 2.0 are found and available on the following website: http://blast.wustl.edu.

As referred to above, "under stringent conditions" means that hybridization takes place under moderately or highly stringent conditions. To be specific, the moderately stringent conditions can be easily determined by those having ordinary skill in the art on the basis of, for example, the length of DNA. Basic conditions are described in Sambrook, et al., *Molecular Cloning: A Laboratory Manual*, 3rd ed., ch. 6-7, Cold Spring Harbor Laboratory Press, 2001. The moderately stringent conditions include hybridization under the conditions of preferably 1×SSC to 6×SSC at 42° C. to 55° C., more preferably 1×SSC to 3×SSC at 45° C. to 50° C., most preferably 2×SSC at 50° C. In the case of using a hybridization solution containing, for example, about 50% formamide, a temperature around 5 to 15° C. lower than the foregoing should be adopted. Washing is also carried out under the conditions of 0.5×SSC to 6×SSC at 40° C. to 60° C. In the process of hybridization and washing, generally 0.05% to 0.2% SDS, preferably about 0.1% SDS, may be added. Likewise, the highly stringent conditions can be easily determined by those having ordinary skill in the art on the basis of, for example, the length of DNA. Generally, the highly stringent (high stringent) conditions include hybridization and/or washing at a higher temperature and/or a lower salt concentration than those adopted under the moderately stringent conditions. For example, hybridization is carried out under the conditions of 0.1×SSC to 2×SSC at 55° C. to 65° C., more preferably 0.1×SSC to 1×SSC at 60° C. to 65° C., most preferably 0.2×SSC at 63° C. Washing is carried out under the conditions of 0.2×SSC to 2×SSC at 50° C. to 68° C., more preferably 0.2×SSC at 60 to 65° C.

Antigens may be obtained by separating and purifying them from a quail egg yolk using a combination of protein purification methods well known to those skilled in the art. Also, antigens may be obtained by expressing them as recombinant proteins using a genetic recombination technique well known to those skilled in the art and by separating and purifying them using protein purification methods well known to those skilled in the art.

Exemplary protein purification methods include, but are not limited to: solubility-based purification methods such as salt precipitation and solvent precipitation; purification methods based on molecular weight difference, such as dialysis, ultrafiltration, gel filtration and SDS-PAGE; charge-based purification methods such as ion exchange chromatography and hydroxylapatite chromatography; specific affinity-based purification methods such as affinity chromatography; purification methods based on hydrophobicity difference, such as reverse-phase high-performance liquid chromatography; and purification methods based on isoelectric point difference, such as isoelectric focusing.

Preparation of a protein by a genetic recombination technique is carried out by preparing an expression vector comprising an antigen-encoding nucleic acid, introducing the expression vector into appropriate host cells by gene transfer or genetic transformation, culturing the host cells under suitable conditions for expression of a recombinant protein, and recovering the recombinant protein expressed in the host cells.

The "vector" refers to a nucleic acid that can be used to introduce a nucleic acid attached thereto into host cells. The "expression vector" is a vector that can induce the expression of a protein encoded by a nucleic acid introduced therethrough. Exemplary vectors include plasmid vectors and viral vectors. Those skilled in the art can select an appropriate expression vector for the expression of a recombinant protein depending on the type of host cells to be used.

The "host cells" refers to cells that undergo gene transfer or genetic transformation by a vector. The host cells can be appropriately selected by those skilled in the art depending on the type of the vector to be used. The host cells can be derived from prokaryotes such as *E. coli*. When prokaryotic cells like *E coli.* are used as host cells, the antigen of the present invention may be designed to contain an N-terminal methionine residue in order to facilitate the expression of a recombinant protein in the prokaryotic cells. The N-terminal methionine can be cleaved from the recombinant protein after expression. Also, the host cells may be eukaryote-derived cells, such as single-cell eukaryotes like yeast, plant cells and animal cells (e.g., human cells, monkey cells, hamster cells, rat cells, murine cells or insect cells).

Gene transfer or transformation of an expression vector into host cells can be carried out as appropriate by following a technique known to those skilled in the art. Those skilled in the art can make possible the expression of a recombinant protein by selecting suitable conditions for the expression of the recombinant protein as appropriate depending on the type of host cells and culturing the host cells under the selected conditions. Then, those skilled in the art can homogenize the host cells having the expressed recombinant protein, and separate and purify an antigen expressed as the recombinant protein from the resulting homogenate by using an appropriate combination of such protein purification methods as mentioned above.

Diagnosis Kit and Method

The present invention provides a method for providing an indicator for diagnosing an allergy to a quail egg, the method comprising the steps of:
(i) contacting a sample obtained from a subject with an antigen in spot 1 or an antigen in spot 2 as mentioned above;
(ii) detecting binding between an IgE antibody present in the sample from the subject and the antigen; and
(iii) when the binding between the IgE antibody in the subject and the antigen is detected, an indicator of the fact that the subject is allergic to a quail egg is provided.

The sample obtained from a subject is a solution containing an Ig antibody, preferably an IgE antibody, as collected from the subject. Examples of such solutions include, but are not limited to, blood, saliva, sputum, snivel, urine, sweat, and tear. The sample obtained from the subject may be subjected to pretreatment for increasing the concentration of an Ig antibody in the sample before being contacted with an antigen. The pretreatment of a sample may involve, for example, collection of the serum from the blood. In a particularly preferred mode, the step (i) mentioned above is carried out by contacting an IgE antibody present in the serum obtained from a subject with an antigen.

Detection of contact and binding between the sample obtained from a subject and an antigen can be carried out by using a known method. Examples of such methods that can be used include detection by ELISA (Enzyme-Linked Immunosorbent Assay), sandwich immunoassay, immunoblotting, or immunoprecipitation. These are all techniques for detecting binding between an IgE antibody from a subject and an antigen by contacting and binding the IgE antibody from a subject with the antigen, allowing an enzymatically labelled secondary antibody to act on the IgE antibody specifically bound to the antigen, and adding an enzyme substrate (generally, chromogenic or luminescent reagent) to detect an enzymatic reaction product. Also, detection by a measurement method that permits the analysis of binding between an antigen and an IgE antibody, such as surface plasmon resonance (SPR), can be used.

The antigen may be provided as an isolated antigen in a state immobilized to a carrier. In this case, the steps (i) and (ii) mentioned above can be carried out using ELISA, sandwich immunoassay, immunochromatography, surface plasmon resonance, or the like. Also, the step (i) mentioned above can be carried out by contacting the sample obtained from a subject with an antigen-immobilized surface. The isolated antigen may be obtained by separating and purifying it from a quail egg using a combination of protein purification methods well known to those skilled in the art, or by preparing it using a genetic recombination technique.

The antigen may be detected by immunoblotting in a state separated by two-dimensional electrophoresis. The two-dimensional electrophoresis is a technique for separating a protein sample by performing isoelectric focusing in the first dimension and performing SDS-PAGE (SDS-polyacrylamide gel electrophoresis) in the second dimension. The conditions for two-dimensional electrophoresis are not particularly limited as long as the conditions permit the separation of the antigen of the present invention. For example, the conditions for two-dimensional electrophoresis as described above in the subsection titled "Identification of antigens" can be adopted. Also, the 2D electrophoresis conditions may be defined by reference to the disclosures in PTLs 1 to 4 mentioned above. For example, two-dimensional electrophoresis can be carried out under the conditions that satisfy at least one selected from the group consisting of the following requirements:

(A) the isoelectric focusing gels used in the first dimension should have a gel-strip length of 5 to 10 cm and a gel pH range of 3 to 10, and the pH gradient of the gels in the direction of electrophoresis should be as follows: where the gel-strip length up to pH 5 is taken as "a", that length from pH 5 to 7 as "b", and that length above pH 7 as "c", the relations "a<b" and "b>c" are satisfied;

(B) in the case of (A), when the total gel-strip length is taken as 1, "a" should be in the range of 0.15 to 0.3, "b" should be in the range of 0.4 to 0.7, and "c" should be in the range of 0.15 to 0.3;

(C) in the first dimensional isoelectric focusing, a constant voltage step should be performed by applying a constant voltage ranging from 100 V to 600 V per gel strip containing a sample, and after the current variation width during electrophoresis for 30 minutes falls within the range of 5 µA, a voltage-increasing step should be started at which the voltage is increased from the aforementioned constant voltage;

(D) in the case of (C), the final voltage at the voltage-increasing step should be in the range of 3000 V to 6000 V;

(E) the isoelectric focusing gels used in the first dimension should have a longitudinal gel-strip length of 5 to 10 cm, and the electrophoresis gels used in the second dimension should have a gel concentration at the distal end in the direction of electrophoresis, which is in the range of 3 to 6%; and (F) in the case of (E), the electrophoresis gels used in the second dimension should have a gel concentration at the proximal end in the direction of electrophoresis, which is set to a higher value than that at the distal end.

The antigen in spot 1 or the antigen in spot 2 as mentioned above is an antigen that is capable of specifically binding to an IgE antibody in a patient with an allergy to a quail egg. Therefore, when binding between the IgE antibody in a subject and the antigen is detected, an indicator of the fact that the subject is allergic to a quail egg is provided.

The present invention further provides a kit for diagnosing an allergy to a quail egg, the kit comprising an antigen in spot 1 or an antigen in spot 2 as mentioned above. The diagnosis kit of this invention may be used in the aforementioned method for providing an indicator for diagnosing an allergy to a quail egg, or in a diagnosis method as described later. The diagnosis kit of this invention may comprise not only the antigen in spot 1 or the antigen in spot 2 as mentioned above, but also an anti-IgE antibody labeled with an enzyme and a chromogenic or luminescent substrate serving as a substrate for said enzyme. Also, a fluorescent-labeled anti-IgE antibody may be used. In the diagnosis kit of this invention, the antigen may be provided in a state immobilized to a carrier. The diagnosis kit of this invention may also be provided together with instructions on the procedure for diagnosis or a package containing said instructions.

In another mode, the diagnosis kit includes a companion diagnostic agent for an allergy to a quail egg. The companion diagnostic agent is used to analyze the reactivity of a pharmaceutical product for the purpose of identifying a patient in which the pharmaceutical product is expected to work or a patient at risk for serious side effects from the pharmaceutical product, or optimizing a therapy using the pharmaceutical product (e.g., determining a dosage regimen, or judging whether to withdraw the medication).

The present invention further provides a composition for diagnosing an allergy to a quail egg, the composition comprising an antigen in spot 1 or an antigen in spot 2 as mentioned above. The diagnosis composition of this invention can be used in a diagnosis method as described below. The diagnosis composition of this invention may further comprise a pharmaceutically acceptable carrier and/or additives commonly used with the antigen of this invention depending on the need.

In one mode, the present invention provides a method for diagnosing an allergy to a quail egg in a subject, the method comprising:
(i) contacting a sample obtained from the subject with an antigen in spot 1 or an antigen in spot 2 as mentioned above;
(ii) detecting binding between an IgE antibody present in the sample from the subject and the antigen; and
(iii) when the binding between the IgE antibody in the subject and the antigen is detected, diagnosing the subject as being allergic to a quail egg. In this method, the steps (i) and (ii) are performed as described above regarding the corresponding steps of the method for providing an indicator for diagnosing an allergy to a quail egg.

In another mode, the present invention provides a method for diagnosing an allergy to a quail egg in a subject, the method comprising administering an antigen in spot 1 or an antigen in spot 2 as mentioned above to the subject. This method may be performed in the form of a skin test characterized by applying the antigen onto the skin. Examples of the skin test include various forms of tests, such as: a prick test in which a diagnosis composition is applied onto the skin and then a tiny prick to such an extent as not to provoke bleeding is made in the skin to allow an antigen to penetrate the skin, thereby observing a skin reaction; a scratch test in which a diagnosis composition is applied onto the skin and then the skin is lightly scratched to observe a reaction; a patch test in which a diagnosis composition in the form of cream, ointment, etc. is applied onto the skin to observe a reaction; and an intracutaneous test in which an antigen is administered intracutaneously to observe a reaction. If a skin reaction such as swelling occurs in a skin portion to which the antigen has been applied, the subject of interest is diagnosed as having an allergy to a quail egg. The amount of the antigen to be applied to the skin in such tests can be, for example, not more than 100 μg per dose.

In yet another mode, the present invention provides an antigen in spot 1 or an antigen in spot 2, as mentioned above, intended for use in the diagnosis of an allergy to a quail egg.

In still another mode, the present invention provides use of an antigen in spot 1 or an antigen in spot 2, as mentioned above, for the production of a diagnostic agent for an allergy to a quail egg.

Pharmaceutical Composition and Treatment Method

The present invention provides a pharmaceutical composition comprising an antigen in spot 1 or an antigen in spot 2 as mentioned above.

In one mode, the aforementioned pharmaceutical composition is used for the treatment of an allergy to a quail egg.

The present invention also provides a method for treating an allergy to a quail egg, the method comprising administering an antigen in spot 1 or an antigen in spot 2 as mentioned above to a patient in need thereof.

In another mode, the present invention provides an antigen in spot 1 or an antigen in spot 2, as mentioned above, intended for use in the diagnosis of an allergy to a quail egg. In yet another mode, this invention provides use of an antigen in spot 1 or an antigen in spot 2, as mentioned above, for the production of a diagnostic agent for an allergy to a quail egg.

In the process of allergy treatment, a hyposensitization therapy aiming to induce immunological tolerance by administering an antigen to a patient is often adopted. The antigen in spot 1 or the antigen in spot 2 as mentioned above can be used as an active component for a hyposensitization therapy or a load test for an allergy to a quail egg.

The pharmaceutical composition of the present invention can be administered by common administration routes. Examples of common administration routes include oral, sublingual, percutaneous, intracutaneous, subcutaneous, intravascular, intranasal, intramuscular, and intraperitoneal administrations.

The pharmaceutical composition of the present invention can be used as a pharmaceutical composition to which a commonly used pharmaceutically acceptable adjuvant or excipient or any other additives (e.g., stabilizer, solubilizer, emulsifier, buffer, preservative, colorant) are added by a conventional method together with the antigen of this invention depending on the need. The dosage form of the pharmaceutical composition can be selected by those skilled in the art as appropriate depending on the administration route. The pharmaceutical composition can be in the form of, for example, tablet, capsule, troche, sublingual tablet, parenteral injection, intranasal spray, poultice, solution, cream, or lotion. The administration dose, frequency and/or period of the pharmaceutical composition of this invention can be selected by a physician as appropriate depending on the administration route and the patient's condition and characteristics such as age and body weight. For example, the pharmaceutical composition may be administered to an adult patient at a dose of not more than 100 μg per dose. The administration interval can be, for example, once daily, once weekly, twice weekly, once per three months or so. The administration period can be, for example, several weeks to several years. The pharmaceutical composition may be administered in such a manner that the dose is increased in incremental steps over the administration period.

Tester

The present invention provides a tester comprising an antibody against at least one of an antigen in spot 1 or an antigen in spot 2 as mentioned above.

The antibody can be prepared by a conventional method. For example, the antibody may be prepared by immunizing a mammal such as rabbit with the antigen in spot 1 or the antigen in spot 2 as mentioned above. The antibody may be an Ig antibody, a polyclonal antibody, a monoclonal antibody, or an antigen-binding fragment thereof (e.g., Fab, F(ab')2, Fab').

Further, in the aforementioned tester, the antibody may be provided in a form bound to a carrier. The type of the carrier is not particularly limited as long as it is usable for detection of binding between an antibody and an antigen. Any given carrier known to those skilled in the art can be used.

Examples of a method for determining the presence or absence of an antigen include the following:

a method in which a prepared tester comprising an Ig antibody is contacted with a sample obtained from a food, etc., ELISA or the like method is used to detect whether there is a binding between the Ig antibody and an antigen in the sample, and if the binding between the Ig antibody and the antigen is detected, it is determined that the antibody is present in the food, etc. of interest; and a method in which a food is infiltrated into a filter paper or the like and an antibody solution is reacted with the filter paper to detect an antigen present in the food.

Another mode of the present invention includes a tester for determining the presence or absence of a causative antigen of an allergy to a quail egg in an object of interest, the tester comprising a primer having a nucleotide sequence complementary to at least one of the nucleotide sequence of SEQ ID NO:17 or the nucleotide sequence of SEQ ID NO:23. For example, the primer has, without limitation, a nucleotide sequence complementary to preferably 25, 20, 15 or 12 residues at the 5' end of at least one of the nucleotide sequence of SEQ ID NO:17 or the nucleotide sequence of SEQ ID NO:23.

Examples of a method for determining the presence or absence of an antigen include a method in which a prepared tester comprising a primer is contacted with DNA or mRNA extracted from a food material to detect the presence or absence of antigen DNA, thereby testing to determine whether the food material is of an edible variety for patients with an allergy to a quail egg.

In one mode, the aforementioned tester is used to determine the presence or absence of an antigen in foods or in products of interest in a food production line. The tester may also be used for quality inspection of production lines and pre-shipment products by manufacturers, or may be used for self-checking of the presence or absence of an antigen in a food of interest by consumers.

Allergen-Free Food and the Like

The present invention provides a quail egg or a processed product of quail egg which are characterized by being devoid of an antigen in spot 1 or an antigen in spot 2 as mentioned above.

The method used to remove the antigen of the present invention from a quail egg or a processed product of quail egg is not limited. Removal of the inventive antigen can be done by any method, as long as the method permits removal of said antigen.

For example, the quail egg devoid of the antigen of the present invention may be obtained by preparing a quail egg in which the expression of the antigen of this invention is knocked out, using a gene knock-out technique.

As the gene knock-out technique, there can be used any methods known to those skilled in the art. For example, Oishi, et al. (*Scientific Reports*, Vol. 6, Article number: 23980, 2016, doi:10.1038/srep23980) describes that the genome editing technique CRISPER/Cas9 is applied to chicken primordial germ cells to obtain individual animals deficient in ovomucoid gene. The quail egg devoid of the antigen of this invention may also be obtained by applying the same technique as above to a quail.

The processed product of quail egg devoid of the antigen of the present invention may be a processed product prepared using as a source ingredient the quail egg devoid of the antigen of this invention. In the case of using an ordinary quail egg as a source ingredient, a treatment for removing the antigen of this invention is performed before or after preparation of a processed product of quail egg. The method used to remove the antigen of this invention from a processed product of quail egg prepared using an ordinary quail egg used as a source ingredient can be exemplified by a method for removal of an antigen by high-pressure treatment and elution of an antigenic protein with a neutral salt solution as described in Japanese Patent No. JP 3653132, and a method for removing a protein component from a food by applying a high-temperature steam.

EXAMPLES

The following describes examples of the present invention. The technical scope of this invention is not limited by these examples.

Example 1: Confirmation of a Protein Pattern

Proteins present in a quail egg were investigated using a two-dimensional electrophoresis method described below.

Protein Extraction

A commercially available quail egg was purchased and divided into egg white and egg yolk. 1000 μL of a mammalian cell lysis kit (MCL1; produced by Sigma-Aldrich), which is a protein extraction reagent, was added to 100 μL each of the egg white and egg yolk, and the mixture was shaken and extracted on a vortex mixer at 25° C. for 10 minutes. After the shaking and extraction, a liquid protein extract was collected. The constituents of the mammalian cell lysis kit MCL1 are as mentioned below.

50 mM Tris-HCl pH 7.5
1 mM EDTA (ethylenediaminetriacetic acid)
250 mM NaCl
0.1% (w/v) SDS (sodium dodecyl sulfate)
0.5% (w/v) sodium deoxycholate
1% (v/v) Igepal CA-630 ((Octylphenoxy)polyethoxyethanol surfactant produced by Sigma-Aldrich)
Moderate amount of protease inhibitor Thereafter, the precipitation procedure was repeated twice using a 2D-CleanUP Kit (produced by GE). In the first round of precipitation, the collected liquid protein extract was precipitated by adding TCA (trichloroacetic acid) thereto and the precipitated product produced by this procedure (TCA-precipitated product) was collected. In the second round of precipitation, the TCA-precipitated product collected above was further precipitated by adding acetone thereto and the precipitated product (sample) produced by this procedure was collected.

Preparation of a Sample Solution

Part of the collected sample (30m on a protein weight basis) was dissolved in 150 μL of a DeStreak Rehydration Solution (produced by GE), which is a swelling buffer for first-dimensional isoelectric focusing gels, thereby obtaining a sample solution for first-dimensional isoelectric focusing (sample solution for swelling). The constituents of the DeStreak Rehydration Solution are as mentioned below.

7M thiourea
2M urea
4% (w/v) CHAPS (3-[(3-cholamidopropyl)dimethylammonio]propanesulfonate)
0.5% (v/v) IPG buffer; produced by GE
Moderate amount of BPB (bromophenol blue)

Penetration of the Sample into First-Dimensional Isoelectric Focusing Gels

First-dimensional isoelectric focusing gel strips (Immobiline Drystrip IPG gels (pH3-10NL); produced by GE) were immersed in 140 μL of the foregoing sample solution for first-dimensional isoelectric focusing (sample solution for swelling) and impregnated with the solution at room temperature overnight.

In this example, an IPGphor electrophoresis system produced by GE was used.

An electrophoresis tray was filled with silicone oil. Filter paper moisten with water was positioned at both ends of the gel strips impregnated with the sample, and the gel strips were set in the electrophoresis tray such that the gels were covered with silicone oil. Electrodes were placed on the gel strips with the filter paper intervening therebetween.

The maximum current of the isoelectric focusing system was set to 75 μA per gel strip, and the first-dimensional isoelectric focusing was carried out according to the following voltage program: (1) a constant voltage step was performed at a constant voltage of 300 V until the volt-hours reached 750 Vhr (the current variation width during electrophoresis for 30 minutes before the end of this step was 5 μA); (2) the voltage was increased gradually to 1000 V for 300 Vhr; (3) the voltage was further increased gradually to 5000 V for 4500 Vhr; and then (4) the voltage was held at a constant voltage of 5000 V until the total Vhr reached 12000.

SDS Equilibration of Isoelectric Focusing Gels

After the aforementioned first-dimensional isoelectric focusing was done, the gel strips were taken out of the isoelectric focusing system, immersed in an equilibration buffer containing a reducing agent, and shaken at room temperature for 15 minutes. The constituents of the equilibration buffer containing a reducing agent are as mentioned below.

100 mM Tris-HCl (pH 8.0)
6 M urea

30% (v/v) glycerol
2% (w/v) SDS
1% (w/v) DTT

Next, the equilibration buffer containing a reducing agent was removed, and then the gel strips were immersed in an equilibration buffer containing an alkylating agent and shaken at room temperature for 15 minutes to obtain SDS-equilibrated gels. The constituents of the equilibration buffer containing an alkylating agent are as mentioned below.

100 mM Tris-HCl (pH 8.0)
6 M urea
30% (v/v) glycerol
2% (w/v) SDS
2.5% (w/v) iodoacetamide Second-Dimensional SDS-PAGE In this example, the XCell SureLock Mini-Cell electrophoresis system produced by Life Technologies was used. The second-dimensional electrophoresis gels used were NuPAGE 4-12% Bis-Tris Gels produced by Life Technologies. Also, an electrophoresis buffer composed of the following constituents was prepared and used.

50 mM MOPS
50 mM Tris base
0.1% (w/v) SDS
1 mM EDTA

Further, an agarose solution for gel adhesion was used in this example, which was prepared by dissolving 0.5% (w/v) Agarose S (produced by Nippon Gene Co., Ltd.) and a moderate amount of BPB (bromophenol blue) in the electrophoresis buffer.

SDS-PAGE wells were washed well with the electrophoresis buffer, and then the buffer used for the washing was removed. The washed wells were charged with the fully dissolved agarose solution for gel adhesion. Next, the SDS-equilibrated gel strips were immersed in agarose and closely adhered to second-dimensional electrophoresis gels using tweezers. After it was confirmed that agarose was fully fixed with the gels being closely adhered to each other, electrophoresis was performed at a constant voltage of 200 V for about 45 minutes.

Fluorescent Staining of Gels

The gels were fluorescently stained with SYPRO Ruby (produced by Life Technologies).

First, an airtight container to be used was washed well in advance with 98% (v/v) ethanol. The electrophoresed second-dimensional electrophoresis gel strips were taken out of the SDS-PAGE system, placed onto the washed airtight container, and treated twice by immersion in 50% (v/v) methanol and 7% (v/v) aqueous solution containing acetic acid for 30 minutes. Then, a further immersion treatment was done for 10 minutes, with the solution being replaced by water. Next, the second-dimensional electrophoresis gel strips were immersed in 40 mL of SYPRO Ruby and shaken at room temperature overnight. Thereafter, the SYPRO Ruby was removed, and then the second-dimensional electrophoresis gel strips were washed with water and shaken in 10% (v/v) methanol and 7% (v/v) aqueous solution containing acetic acid for 30 minutes. Further shaking was done for at least 30 minutes, with the solution being replaced by water.

Analysis

The second-dimensional electrophoresis gels obtained through the foregoing series of treatments were subjected to fluorescent image scanning on Typhoon 9400 (produced by GE). The results of the two-dimensional electrophoresis are shown in FIG. 1. Molecular weight marker bands are found at the left of the panels. The positions of the bands denote particular molecular weights (in KDa).

Example 2: Identification of Antigens by Immunoblotting

Identification of antigens by immunoblotting was carried out by taking all the steps up to the step of "Second-dimensional SDS-PAGE" as described above in Example 1, followed by the steps of "Transfer to membrane", "Immunoblotting" and "Analysis" as described below.

Transfer to Membrane

Transfer to membrane was done using the following transfer system and transfer buffer.

Transfer system: XCell SureLock Mini-Cell and XCell II Blot Module (produced by Life Technologies)

Transfer buffer: NuPAGE Transfer Buffer (20×) (produced by Life Technologies), used in a form diluted 20-fold with milliQ water.

To be specific, proteins in the two-dimensional electrophoresis gels were transferred to a membrane (PVDF membrane) according to the following procedure.

(1) The PVDF membrane was immersed in 100% methanol followed by milliQ water, and then moved into the transfer buffer to hydrophilize the PVDF membrane.

(2) After sponge, filter paper, the gels treated by second-dimensional SDS-PAGE, the hydrophilized PVDF membrane, filter paper, and sponge were put in place in this order, the transfer system was energized at a constant voltage of 30 V for one hour.

Immunoblotting

Immunoblotting of the membrane was carried out using, as a primary antibody, a serum sample from a patient with a quail egg allergy or a serum sample from a healthy subject. The quail egg-allergic patient had an allergic reaction, not to chicken egg, but to quail egg only.

Immunoblotting of the membrane was carried out according to the following procedure.

(1) The transferred membrane was shaken in a 5% skim milk/PBST solution (a PBS buffer containing 3% Tween 20 nonionic surfactant) at room temperature for one hour.

(2) The membrane was left to stand in a solution of 3% primary antibody serum in 5% skim milk/PBST at room temperature for one hour.

(3) The membrane was washed with a PBST solution (5 min.×3 times).

(4) The membrane was left to stand in a 1:2500 dilution of the secondary antibody, anti-human IgE-HRP (horseradish peroxidase), with a 3% skim milk/PBST solution at room temperature for one hour.

(5) The membrane was washed with a PBST solution (5 min.×3 times).

(6) The membrane was left to stand in Pierce Western Blotting Substrate Plus (produced by Thermo Fisher Scientific) for 5 minutes.

Analysis

The membrane obtained through the foregoing series of treatments was subjected to fluorescent image scanning on Typhoon 9400 (produced by GE).

Figure 2:
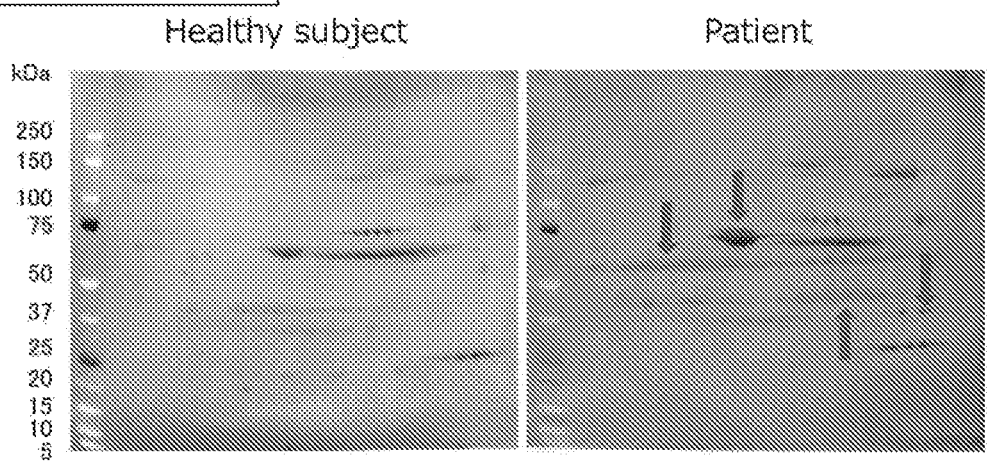
FIG. 2 is a set of photos showing the results of immunoblotting performed for 2D electrophoresis patterns of proteins present in quail egg yolk and white. The upper set of photos shows immunoblots of quail egg yolk proteins, and the lower set of photos shows immunoblots of quail egg white proteins. For each set of photos, the right panel shows an immunoblot obtained using the serum from a quail egg-allergic patient, and the left panel shows an immunoblot obtained using the serum from a healthy subject. The arrows show the different protein spots containing proteins with which the quail egg-allergic patient's serum specifically reacted.
Figure 2:
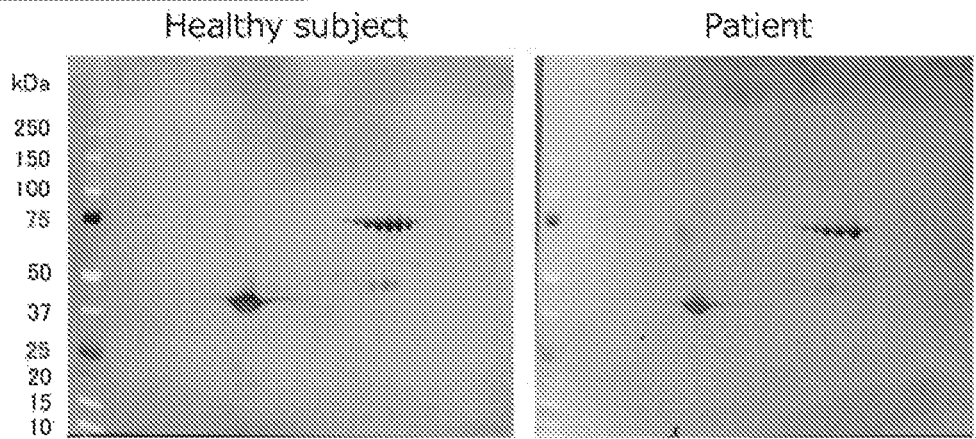

The immunoblots obtained with the serum from the quail egg-allergic patient were compared with those obtained with the control serum from the healthy subject. By immunoblotting against a quail egg yolk using the serum from the quail egg-allergic patient, four different protein spots were detected, which were not observed by immunoblotting with the serum from the healthy subject (FIG. 2).

Example 3: Inhibition Test

In order to confirm that the protein spots detected by immunoblotting with the serum from the quail egg-allergic patient in Example 2 are protein spots specific to quail egg yolk, an inhibition test was done using a chicken egg yolk before the immunoblotting in Example 2.

To be specific, before the immunoblotting step (2) in Example 2, an extract of MCL1 from a chicken egg yolk (1 mg by protein content) was mixed with 75 μL of the serum, and the mixture was left to stand at room temperature for one hour. The resulting mixture was used as a serum sample to perform immunoblotting in the same manner as in Example 2.

Figure 3:
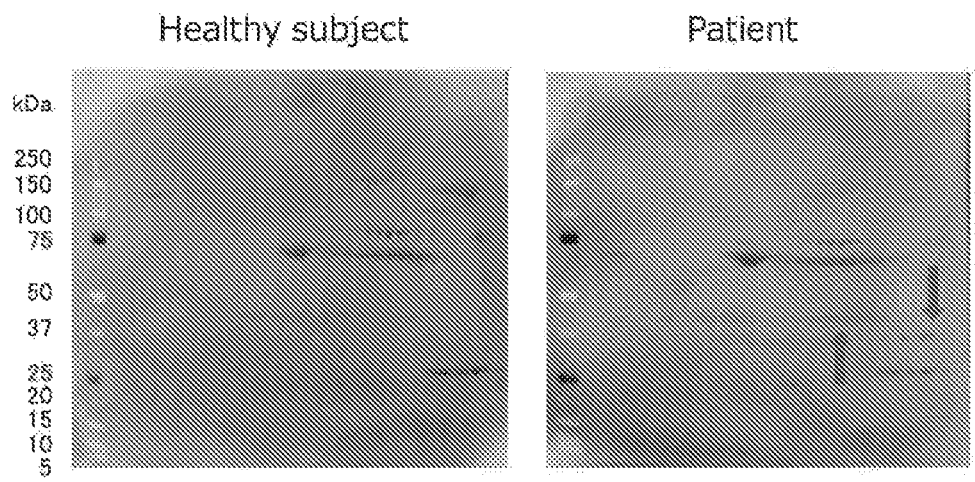
FIG. 3 is a set of photos of immunoblots showing the results of an inhibition test. The upper right panel shows an immunoblot obtained for a 2D electrophoresis pattern of quail egg yolk proteins using a quail egg-allergic patient's serum inhibited with a chicken egg yolk. The arrows show the different protein spots containing proteins with which the quail egg-allergic patient's serum specifically reacted. The upper left panel shows an immunoblot obtained for a 2D electrophoresis pattern of quail egg yolk proteins using a healthy subject's serum inhibited with a chicken egg yolk. The lower right panel shows an immunoblot obtained for a 2D electrophoresis pattern of chicken egg yolk proteins using a quail egg-allergic patient's serum inhibited with a quail egg yolk. The lower left panel shows an immunoblot obtained for a 2D electrophoresis pattern of chicken egg yolk proteins using a healthy subject's serum inhibited with a quail egg yolk.
Figure 3:
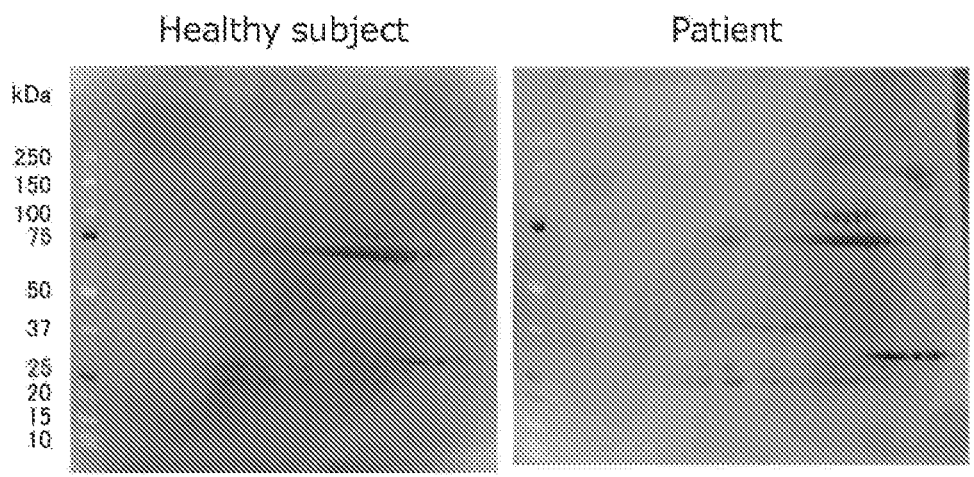

The result revealed that one protein spot with an isoelectric point of 5 to 9 and a molecular weight of around 45 kDa, and another protein spot with an isoelectric point of 7 to 12 and a MW of around 35 kDa suggest specific binding of the quail egg-allergic patient's serum to quail egg yolk protein (upper immunoblot panel of FIG. 3). In other words, it was demonstrated that these two protein spots represent antigens of quail egg allergy.

Further, for the purpose of ensuring more accuracy, a chicken egg yolk was subjected to two-dimensional electrophoresis, followed by immunoblotting using a serum sample inhibited with a quail egg yolk.

To be specific, a chicken egg yolk was subjected to two-dimensional electrophoresis by the same procedure as in Example 1. And, before the immunoblotting step (2) in Example 2, an extract of MCL1 from a quail egg yolk (1 mg by protein content) was mixed with 75 μL of the serum, and the mixture was left to stand at room temperature for one hour. The resulting mixture was used as a serum sample to perform immunoblotting in the same manner as in Example 2.

The immunoblot results obtained with the quail egg-allergic patient's serum treated in advance with a quail egg yolk showed the same pattern as those obtained with a healthy subject's serum—no protein spot was found which is specific to quail egg-allergic patients (lower immunoblot panel of FIG. 3).

Example 4: Mass Spectroscopy

The amino acid sequences of the antigens that form the two protein spots identified in Example 3 were identified by mass spectroscopy.

To be specific, protein extraction and mass spectroscopy were done by the following procedure.

(1) A quail egg yolk was subjected to protein extraction, two-dimensional electrophoresis and transfer to membrane by following the procedures described in Example 2, and the resulting membrane was stained by shaking in a solution of 0.008% Direct blue in 40% ethanol and 10% acetic acid.

(2) Then, the membrane was decolorized by repeating a 5-minute treatment with 40% ethanol and 10% acetic acid three times, washed with water for 5 minutes, and then dried by air.

(3) A protein spot of interest was cut out with a clean cutter blade and put into a centrifugal tube. The cut membrane was subjected to hydrophilization with 50 μL of methanol, followed by washing with 100 μL of water twice and then centrifugal cleaning. Thereafter, 20 μL of 20 mM $NH_4HCO_3$ and 50% acetonitrile were added.

(4) 1 μL of 1 pmol/μL lysyl endopeptidase (produced by WAKO) was added, and the solution was left to stand at 37° C. for 60 minutes and then collected in a new centrifugal tube. After 20 μL of 20 mM $NH_4HCO_3$ and 70% acetonitrile were added to the membrane, the membrane was immersed therein at room temperature for 10 minutes, and the resulting solution was further collected. The solution was dissolved with 0.1% formic acid and 10 μL of 4% acetonitrile and transferred to a tube.

(5) The collected solution was dried under reduced pressure, dissolved with 15 μL of solution A (a 0.1% formic acid/4% acetonitrile solution), and analyzed by mass spectroscopy (ESI-TOF5600, produced by AB Sciex).

(6) Identification of proteins based on the MS data obtained with the mass spectrometer was done by searching the NCBI database.

Results

The mass spectroscopic analysis of the protein spot appearing in the region with a molecular weight of 35 kDa to 50 kDa and an isoelectric point of 5 to 9 on the two-dimensional electrophoresis under the conditions described in a previous example led to the detection of the amino acid sequences of SEQ ID NOs:1-4 and 6-16. When the MS data obtained for this protein spot with the mass spectrometer were analyzed using the NCBI database, the proteins in this spot were identified as different portions of vitellogenin-1 protein (SEQ ID NO:18) derived from Japanese quail (*Coturnix japonica*).

Likewise, the mass spectroscopic analysis of the protein spot appearing in the region with a molecular weight of 30 kDa to 50 kDa and an isoelectric point of 7 to 12 on the two-dimensional electrophoresis under the conditions described in a previous example led to the detection of the amino acid sequences of SEQ ID NOs:19 to 22. When the MS data obtained for this protein spot with the mass spectrometer were analyzed using the NCBI database, the proteins in this spot were identified as different portions of vitellogenin-2 protein (SEQ ID NO:24) derived from Japanese quail (*Coturnix japonica*).

INDUSTRIAL APPLICABILITY

The present invention can provide novel antigens of an allergy to a quail egg, kits and methods for diagnosing an allergy to a quail egg, pharmaceutical compositions comprising such an antigen, quail eggs or processed products of quail egg which are devoid of such an antigen, and testers for determining the presence or absence of such an antigen.

The invention claimed is:

1. A quail-derived antigen, wherein said quail-derived antigen is a protein:
   (1B) comprising at least one amino acid sequence selected from the group consisting of SEQ ID NOs: 1, 4, 6, 8-10, 12-14 and 18; or,
   (2B) comprising at least one amino acid sequence selected from the group consisting of SEQ ID NOs: 19, 21, 22 and 24,
   and is causative of allergy to quail egg,
   wherein said quail-derived antigen is immobilized to a carrier or a surface.

2. The quail-derived antigen of claim 1, wherein the carrier or the surface is for detecting binding between said IgE antibody and said quail-derived antigen through immunoassay.

3. A kit, comprising a quail-derived antigen, wherein said quail-derived antigen is a protein:
   (1B) comprising at least one amino acid sequence selected from the group consisting of SEQ ID NOs: 1, 4, 6, 8-10, 12-14 and 18; or,
   (2B) comprising at least one amino acid sequence selected from the group consisting of SEQ ID NOs: 19, 21-22 and 24,
   and is causative of allergy to quail egg,
   wherein said quail-derived antigen is immobilized to a carrier or a surface.

4. A kit, comprising:
   (i) a quail-derived antigen, wherein said quail-derived antigen is a protein:
      (1B) comprising at least one amino acid sequence selected from the group consisting of SEQ ID NOs: 1, 4, 6, 8-10, 12-14 and 18; or,
      (2B) comprising at least one amino acid sequence selected from the group consisting of SEQ ID NOs: 19, 21-22 and 24,
      and is causative of allergy to quail egg, and,
   (ii) an antibody which detects binding between said quail-derived antigen and an IgE antibody that specifically binds to the quail-derived antigen;
   wherein said quail-derived antigen is immobilized to a carrier or a surface.

5. A kit, comprising:
   (i) a quail-derived antigen, wherein said quail-derived antigen is a protein:
      (1B) comprising at least one amino acid sequence selected from the group consisting of SEQ ID NOs: 1, 4, 6, 8-10, 12-14 and 18; or, (2B) comprising at least one amino acid sequence selected from the group consisting of SEQ ID NOs: 19, 21-22 and 24, and is causative of allergy to quail egg, and, (ii) a secondary antibody specific for IgE antibody that specifically binds to the quail-derived antigen;

wherein said quail-derived antigen is immobilized to a carrier or a surface.

6. A composition comprising a quail-derived antigen, wherein said quail-derived antigen is a protein:

(1B) comprising at least one amino acid sequence selected from the group consisting of SEQ ID NOs: 1, 4, 6, 8-10, 12-14 and 18; or, (2B) comprising at least one amino acid sequence selected from the group consisting of SEQ ID NOs: 19, 21-22 and 24, and is causative of allergy to quail egg, wherein said quail-derived antigen is immobilized to a carrier or a surface.

* * * * *

SEQUENCE LISTING

<160> NUMBER OF SEQ ID NOS: 24

<210> SEQ ID NO 1
<211> LENGTH: 13
<212> TYPE: PRT

```
<213> ORGANISM: Conturnix japonica

<400> SEQUENCE: 1

Ser Phe Lys Pro Val Tyr Thr Asp Val Pro Ile Glu Lys
1               5                   10

<210> SEQ ID NO 2
<211> LENGTH: 15
<212> TYPE: PRT
<213> ORGANISM: Conturnix japonica

<400> SEQUENCE: 2

Thr Phe Ala Val Thr Arg Asn Ile Glu Asp Leu Ala Ala Ser Lys
1               5                   10                  15

<210> SEQ ID NO 3
<211> LENGTH: 15
<212> TYPE: PRT
<213> ORGANISM: Conturnix japonica

<400> SEQUENCE: 3

Met Thr Pro Val Leu Leu Pro Glu Ala Val Pro Asp Ile Met Lys
1               5                   10                  15

<210> SEQ ID NO 4
<211> LENGTH: 9
<212> TYPE: PRT
<213> ORGANISM: Coturnix japonica

<400> SEQUENCE: 4

Lys Ser Val His Ala Ala Phe Ile Lys
1               5

<210> SEQ ID NO 5

<400> SEQUENCE: 5

000

<210> SEQ ID NO 6
<211> LENGTH: 10
<212> TYPE: PRT
<213> ORGANISM: Coturnix japonica

<400> SEQUENCE: 6

Pro Val Tyr Thr Asp Val Pro Ile Glu Lys
1               5                   10

<210> SEQ ID NO 7
<211> LENGTH: 15
<212> TYPE: PRT
<213> ORGANISM: Coturnix japonica

<400> SEQUENCE: 7

Ile Gln Val Thr Ile Gln Ala Gly Asp Gln Ala Pro Thr Lys Met
1               5                   10                  15

<210> SEQ ID NO 8
<211> LENGTH: 14
<212> TYPE: PRT
<213> ORGANISM: Coturnix japonica

<400> SEQUENCE: 8

Ala Leu Pro His Asp Lys Pro Phe Ala Ser Gly Tyr Leu Lys
1               5                   10
```

<210> SEQ ID NO 9
<211> LENGTH: 9
<212> TYPE: PRT
<213> ORGANISM: Coturnix japonica

<400> SEQUENCE: 9

Asp Trp Glu Thr Asn Tyr Asp Phe Lys
1               5

<210> SEQ ID NO 10
<211> LENGTH: 11
<212> TYPE: PRT
<213> ORGANISM: Coturnix japonica

<400> SEQUENCE: 10

Glu Glu Thr Asn Val Ile Thr Val Ser Ser Lys
1               5                   10

<210> SEQ ID NO 11
<211> LENGTH: 14
<212> TYPE: PRT
<213> ORGANISM: Coturnix japonica

<400> SEQUENCE: 11

Ile Gln Val Thr Ile Gln Ala Gly Asp Gln Ala Pro Thr Lys
1               5                   10

<210> SEQ ID NO 12
<211> LENGTH: 16
<212> TYPE: PRT
<213> ORGANISM: Coturnix japonica

<400> SEQUENCE: 12

Asn Thr Ile Gln Asn Val Leu Gln Ala Trp Tyr Gly Pro Asp Glu Lys
1               5                   10                  15

<210> SEQ ID NO 13
<211> LENGTH: 16
<212> TYPE: PRT
<213> ORGANISM: Coturnix japonica

<400> SEQUENCE: 13

Arg Leu Ile Ser Ser Leu Gln Ser Gly Ile Gly Arg Gln Leu Thr Lys
1               5                   10                  15

<210> SEQ ID NO 14
<211> LENGTH: 8
<212> TYPE: PRT
<213> ORGANISM: Coturnix japonica

<400> SEQUENCE: 14

Ser Val His Ala Ala Phe Ile Lys
1               5

<210> SEQ ID NO 15
<211> LENGTH: 13
<212> TYPE: PRT
<213> ORGANISM: Coturnix japonica

<400> SEQUENCE: 15

Thr Phe Ala Val Thr Arg Asn Ile Glu Asp Leu Ala Ala
1               5                   10

```
<210> SEQ ID NO 16
<211> LENGTH: 16
<212> TYPE: PRT
<213> ORGANISM: Coturnix japonica

<400> SEQUENCE: 16

Val Asn Ala His Val Pro Val Asn Val Val Ala Thr Ile Gln Met Lys
1               5                   10                  15

<210> SEQ ID NO 17
<211> LENGTH: 1068
<212> TYPE: DNA
<213> ORGANISM: Coturnix japonica
<220> FEATURE:
<221> NAME/KEY: CDS
<222> LOCATION: (1)..(1068)

<400> SEQUENCE: 17 gac tgg gag act aac tat gac ttc aag gaa atc cta aaa aag ctg tca      48
Asp Trp Glu Thr Asn Tyr Asp Phe Lys Glu Ile Leu Lys Lys Leu Ser
1               5                   10                  15 gac tgg aag gca ctc cct cat gac aaa cct ttt gca tca ggt tac ttg      96
Asp Trp Lys Ala Leu Pro His Asp Lys Pro Phe Ala Ser Gly Tyr Leu
            20                  25                  30 aag atg ttt ggc caa gag ttg atc ttt gga gga ctt gat aaa aac acc     144
Lys Met Phe Gly Gln Glu Leu Ile Phe Gly Gly Leu Asp Lys Asn Thr
        35                  40                  45 atc caa aat gta ctg cag gca tgg tat gga cct gat gaa aaa atc cct     192
Ile Gln Asn Val Leu Gln Ala Trp Tyr Gly Pro Asp Glu Lys Ile Pro
    50                  55                  60 tca ata agg agg tta atc agt agc ctt caa agt ggc ata gga agg caa     240
Ser Ile Arg Arg Leu Ile Ser Ser Leu Gln Ser Gly Ile Gly Arg Gln
65                  70                  75                  80 ttg acc aag gct tta ctg tcc tct gag att cgt cgt att gtg cct acc     288
Leu Thr Lys Ala Leu Leu Ser Ser Glu Ile Arg Arg Ile Val Pro Thr
                85                  90                  95 tgt gtt ggg ttc cca atg gag acc agc ttc tat tac tct tct gtc aca     336
Cys Val Gly Phe Pro Met Glu Thr Ser Phe Tyr Tyr Ser Ser Val Thr
            100                 105                 110 aaa gca gca gga aat gtt caa gtg caa att aca cct tct cca aga tct     384
Lys Ala Ala Gly Asn Val Gln Val Gln Ile Thr Pro Ser Pro Arg Ser
        115                 120                 125 gat ttc aga ttg aca gag tta cta aat tcc aac att agg ctg cga tcc     432
Asp Phe Arg Leu Thr Glu Leu Leu Asn Ser Asn Ile Arg Leu Arg Ser
    130                 135                 140 aaa atg agt ctg agc atg gct aaa cat atg acc ttt gta gtt ggg atc     480
Lys Met Ser Leu Ser Met Ala Lys His Met Thr Phe Val Val Gly Ile
145                 150                 155                 160 aac aca aac ttg att cag gca ggg ttg gaa gca cac acc aaa gta aat     528
Asn Thr Asn Leu Ile Gln Ala Gly Leu Glu Ala His Thr Lys Val Asn
                165                 170                 175 gct cat gta cct gtg aat gtt gtt gcc act att caa atg aag gaa aaa     576
Ala His Val Pro Val Asn Val Val Ala Thr Ile Gln Met Lys Glu Lys
            180                 185                 190 agt atc aaa gct gaa att ccg cca tgc aaa gaa gag act aat gta att     624
Ser Ile Lys Ala Glu Ile Pro Pro Cys Lys Glu Glu Thr Asn Val Ile
        195                 200                 205 act gta agc tct aag aca ttt gct gtt aca cga aat att gaa gac ttg     672
Thr Val Ser Ser Lys Thr Phe Ala Val Thr Arg Asn Ile Glu Asp Leu
    210                 215                 220
```

```
gct gct agt aaa atg act cca gtt ctt cta cct gaa gca gtg cct gac    720
Ala Ala Ser Lys Met Thr Pro Val Leu Leu Pro Glu Ala Val Pro Asp
225             230                 235                 240 ata atg aag atg tcc ttt gac tcg gat tct gca tca ggc gag act gat    768
Ile Met Lys Met Ser Phe Asp Ser Asp Ser Ala Ser Gly Glu Thr Asp
                245                 250                 255 aac atc agg gac aga cag tct gta gaa gat gtt tca tcg gaa aat tcc    816
Asn Ile Arg Asp Arg Gln Ser Val Glu Asp Val Ser Ser Glu Asn Ser
            260                 265                 270 ttc tcc ttt gga cat tct tct tcc tgg aag gag cca ttt gtt cag tcc    864
Phe Ser Phe Gly His Ser Ser Ser Trp Lys Glu Pro Phe Val Gln Ser
        275                 280                 285 atg tgc tct aat gca agt aca ttt ggg gtt caa gtg tgc att gag aag    912
Met Cys Ser Asn Ala Ser Thr Phe Gly Val Gln Val Cys Ile Glu Lys
    290                 295                 300 aaa agt gta cat gca gca ttt atc aaa aat gtg cct ctt tat tac ttt    960
Lys Ser Val His Ala Ala Phe Ile Lys Asn Val Pro Leu Tyr Tyr Phe
305                 310                 315                 320 att gga gaa cat gac ctt aga atg agc ttc aag cca gtc tac aca gat   1008
Ile Gly Glu His Asp Leu Arg Met Ser Phe Lys Pro Val Tyr Thr Asp
                325                 330                 335 gta cct att gaa aaa ata caa gtc aca att cag gca gga gat caa gct   1056
Val Pro Ile Glu Lys Ile Gln Val Thr Ile Gln Ala Gly Asp Gln Ala
            340                 345                 350 cct aca aaa atg                                                    1068
Pro Thr Lys Met
        355

<210> SEQ ID NO 18
<211> LENGTH: 356
<212> TYPE: PRT
<213> ORGANISM: Coturnix japonica

<400> SEQUENCE: 18

Asp Trp Glu Thr Asn Tyr Asp Phe Lys Glu Ile Leu Lys Lys Leu Ser
1               5                   10                  15

Asp Trp Lys Ala Leu Pro His Asp Lys Pro Phe Ala Ser Gly Tyr Leu
            20                  25                  30

Lys Met Phe Gly Gln Glu Leu Ile Phe Gly Gly Leu Asp Lys Asn Thr
        35                  40                  45

Ile Gln Asn Val Leu Gln Ala Trp Tyr Gly Pro Asp Glu Lys Ile Pro
    50                  55                  60

Ser Ile Arg Arg Leu Ile Ser Ser Leu Gln Ser Gly Ile Gly Arg Gln
65                  70                  75                  80

Leu Thr Lys Ala Leu Leu Ser Ser Glu Ile Arg Arg Ile Val Pro Thr
                85                  90                  95

Cys Val Gly Phe Pro Met Glu Thr Ser Phe Tyr Tyr Ser Ser Val Thr
            100                 105                 110

Lys Ala Ala Gly Asn Val Gln Val Gln Ile Thr Pro Ser Pro Arg Ser
        115                 120                 125

Asp Phe Arg Leu Thr Glu Leu Leu Asn Ser Asn Ile Arg Leu Arg Ser
    130                 135                 140

Lys Met Ser Leu Ser Met Ala Lys His Met Thr Phe Val Val Gly Ile
145                 150                 155                 160

Asn Thr Asn Leu Ile Gln Ala Gly Leu Glu Ala His Thr Lys Val Asn
                165                 170                 175
```

```
Ala His Val Pro Val Asn Val Val Ala Thr Ile Gln Met Lys Glu Lys
            180                 185                 190
Ser Ile Lys Ala Glu Ile Pro Pro Cys Lys Glu Glu Thr Asn Val Ile
        195                 200                 205
Thr Val Ser Ser Lys Thr Phe Ala Val Thr Arg Asn Ile Glu Asp Leu
    210                 215                 220
Ala Ala Ser Lys Met Thr Pro Val Leu Leu Pro Glu Ala Val Pro Asp
225                 230                 235                 240
Ile Met Lys Met Ser Phe Asp Ser Asp Ser Ala Ser Gly Glu Thr Asp
                245                 250                 255
Asn Ile Arg Asp Arg Gln Ser Val Glu Asp Val Ser Ser Glu Asn Ser
            260                 265                 270
Phe Ser Phe Gly His Ser Ser Ser Trp Lys Glu Pro Phe Val Gln Ser
        275                 280                 285
Met Cys Ser Asn Ala Ser Thr Phe Gly Val Gln Val Cys Ile Glu Lys
    290                 295                 300
Lys Ser Val His Ala Ala Phe Ile Lys Asn Val Pro Leu Tyr Tyr Phe
305                 310                 315                 320
Ile Gly Glu His Asp Leu Arg Met Ser Phe Lys Pro Val Tyr Thr Asp
                325                 330                 335
Val Pro Ile Glu Lys Ile Gln Val Thr Ile Gln Ala Gly Asp Gln Ala
            340                 345                 350
Pro Thr Lys Met
        355

<210> SEQ ID NO 19
<211> LENGTH: 12
<212> TYPE: PRT
<213> ORGANISM: Conturnix japonica

<400> SEQUENCE: 19

Leu Cys Ala Asp Ala Ser Val Leu Asn Ala His Lys
1               5                   10

<210> SEQ ID NO 20
<211> LENGTH: 10
<212> TYPE: PRT
<213> ORGANISM: Conturnix japonica

<400> SEQUENCE: 20

Thr Val Gln Leu Ala Gly Val Asp Ser Lys
1               5                   10

<210> SEQ ID NO 21
<211> LENGTH: 12
<212> TYPE: PRT
<213> ORGANISM: Coturnix japonica

<400> SEQUENCE: 21

Ala Glu Ala Pro Ser Ala Val Leu Asn Asn Leu Lys
1               5                   10

<210> SEQ ID NO 22
<211> LENGTH: 15
<212> TYPE: PRT
<213> ORGANISM: Coturnix japonica
```

-continued

<400> SEQUENCE: 22

Gly Gly Leu Gln Leu Val Val Phe Ala Asp Thr Asp Ser Val Lys
1               5                   10                  15

<210> SEQ ID NO 23
<211> LENGTH: 1212
<212> TYPE: DNA
<213> ORGANISM: Coturnix japonica
<220> FEATURE:
<221> NAME/KEY: CDS
<222> LOCATION: (1)..(1212)

<400> SEQUENCE: 23

```
act cca gtg tta gct gct ttt ctc cat ggc att agt aac agt aag aag      48
Thr Pro Val Leu Ala Ala Phe Leu His Gly Ile Ser Asn Ser Lys Lys
1               5                   10                  15 aaa gga ggt ctc cag ctt gtg gta ttt gct gat acc gac tct gtc aag      96
Lys Gly Gly Leu Gln Leu Val Val Phe Ala Asp Thr Asp Ser Val Lys
            20                  25                  30 cca cgg atg cag gta ttt gtg aca gac ctc aca gat tca agc aag tgg     144
Pro Arg Met Gln Val Phe Val Thr Asp Leu Thr Asp Ser Ser Lys Trp
        35                  40                  45 aaa ctc tgt gca gat gct tcg gtc ctc aat gct cac aag gca gtg gct     192
Lys Leu Cys Ala Asp Ala Ser Val Leu Asn Ala His Lys Ala Val Ala
    50                  55                  60 tac ctg aaa tgg ggc tgg aat tgc cgg gac tac aag gtt tct act gag     240
Tyr Leu Lys Trp Gly Trp Asn Cys Arg Asp Tyr Lys Val Ser Thr Glu
65                  70                  75                  80 ctg gta act gga cgg ttt gct ggg cat cct gct gca caa gtg aag ctg     288
Leu Val Thr Gly Arg Phe Ala Gly His Pro Ala Ala Gln Val Lys Leu
                85                  90                  95 gag tgg ccc aag gtt cct tca ggt gtc aga tca atg gct gaa tgg ttt     336
Glu Trp Pro Lys Val Pro Ser Gly Val Arg Ser Met Ala Glu Trp Phe
            100                 105                 110 tac agg ttt gtt cct ggg gct gca ttt atg ttg ggt ttc tct gag aga     384
Tyr Arg Phe Val Pro Gly Ala Ala Phe Met Leu Gly Phe Ser Glu Arg
        115                 120                 125 act ggc aag aat cct tct cga caa gcc agg gtg gtt gtg gct cta act     432
Thr Gly Lys Asn Pro Ser Arg Gln Ala Arg Val Val Val Ala Leu Thr
    130                 135                 140 tct cca agg aca tgt gat att gtt gcc aag ctg cct gat ata acc ctc     480
Ser Pro Arg Thr Cys Asp Ile Val Ala Lys Leu Pro Asp Ile Thr Leu
145                 150                 155                 160 tat caa aaa gcc atg agg ctt cct cta tca ctc cct gtg ggt ccg agg     528
Tyr Gln Lys Ala Met Arg Leu Pro Leu Ser Leu Pro Val Gly Pro Arg
                165                 170                 175 atc cca gct tca gag ctg cag cct cca atc tgg aat gtc ttt gct gaa     576
Ile Pro Ala Ser Glu Leu Gln Pro Pro Ile Trp Asn Val Phe Ala Glu
            180                 185                 190 gcc ccc tct gca gtg ctc aac aat ttg aaa gct cgc tgc tca gtt tcg     624
Ala Pro Ser Ala Val Leu Asn Asn Leu Lys Ala Arg Cys Ser Val Ser
        195                 200                 205 cac aac aag atc aca acc ttt aat gga gtc aag ttc aac tac tct atg     672
His Asn Lys Ile Thr Thr Phe Asn Gly Val Lys Phe Asn Tyr Ser Met
    210                 215                 220 cca gga aac tgc tac cac atc ttg gct cag gac tgc agc tct gaa ctt     720
Pro Gly Asn Cys Tyr His Ile Leu Ala Gln Asp Cys Ser Ser Glu Leu
225                 230                 235                 240
```

```
aag ttc ctg gtg acg atg aaa aat gct gat gaa act aca aac ctt aaa         768
Lys Phe Leu Val Thr Met Lys Asn Ala Asp Glu Thr Thr Asn Leu Lys
            245                 250                 255 gcc atc aac atc aag att ggc agt cat gaa att gat atg cat cct gtg         816
Ala Ile Asn Ile Lys Ile Gly Ser His Glu Ile Asp Met His Pro Val
        260                 265                 270 aat gga cag gtg aaa ttg ctg gtg gat ggg gct gag agc ccc aca gcc         864
Asn Gly Gln Val Lys Leu Leu Val Asp Gly Ala Glu Ser Pro Thr Ala
    275                 280                 285 aac att tcc ctc gta tct gct ggt gct tct cta tgg att cgt aat gaa         912
Asn Ile Ser Leu Val Ser Ala Gly Ala Ser Leu Trp Ile Arg Asn Glu
290                 295                 300 aac caa ggg ctt gta ctt gtt ggc cca gcc tat ggt atc gat aca atg         960
Asn Gln Gly Leu Val Leu Val Gly Pro Ala Tyr Gly Ile Asp Thr Met
305                 310                 315                 320 tac ttc aat gga caa aca ttc tgg att caa gtt cct tta tgg atg gca        1008
Tyr Phe Asn Gly Gln Thr Phe Trp Ile Gln Val Pro Leu Trp Met Ala
            325                 330                 335 ggg aaa aca tgt gga atc tgt gga aaa tat gac gca gaa tac aaa cag        1056
Gly Lys Thr Cys Gly Ile Cys Gly Lys Tyr Asp Ala Glu Tyr Lys Gln
        340                 345                 350 gag tat tgg atg ccc aat gga tat tta gct aaa gat tgc gtg agc ttt        1104
Glu Tyr Trp Met Pro Asn Gly Tyr Leu Ala Lys Asp Cys Val Ser Phe
    355                 360                 365 ggt cat tct tgg atc ttg gaa gaa acg ccc tgt aga gga gct tgt aaa        1152
Gly His Ser Trp Ile Leu Glu Glu Thr Pro Cys Arg Gly Ala Cys Lys
370                 375                 380 ctg cat cgt tcg ttt gtg aag ctt gag aag acg gtt cag ctt gcg ggt        1200
Leu His Arg Ser Phe Val Lys Leu Glu Lys Thr Val Gln Leu Ala Gly
385                 390                 395                 400 gtt gat tcc aag                                                         1212
Val Asp Ser Lys <210> SEQ ID NO 24
<211> LENGTH: 404
<212> TYPE: PRT
<213> ORGANISM: Coturnix japonica

<400> SEQUENCE: 24

Thr Pro Val Leu Ala Ala Phe Leu His Gly Ile Ser Asn Ser Lys Lys
1               5                   10                  15

Lys Gly Gly Leu Gln Leu Val Val Phe Ala Asp Thr Asp Ser Val Lys
            20                  25                  30

Pro Arg Met Gln Val Phe Val Thr Asp Leu Thr Asp Ser Ser Lys Trp
        35                  40                  45

Lys Leu Cys Ala Asp Ala Ser Val Leu Asn Ala His Lys Ala Val Ala
    50                  55                  60

Tyr Leu Lys Trp Gly Trp Asn Cys Arg Asp Tyr Lys Val Ser Thr Glu
65                  70                  75                  80

Leu Val Thr Gly Arg Phe Ala Gly His Pro Ala Ala Gln Val Lys Leu
                85                  90                  95

Glu Trp Pro Lys Val Pro Ser Gly Val Arg Ser Met Ala Glu Trp Phe
            100                 105                 110

Tyr Arg Phe Val Pro Gly Ala Ala Phe Met Leu Gly Phe Ser Glu Arg
        115                 120                 125

Thr Gly Lys Asn Pro Ser Arg Gln Ala Arg Val Val Ala Leu Thr
    130                 135                 140
```

-continued

```
Ser Pro Arg Thr Cys Asp Ile Val Ala Lys Leu Pro Asp Ile Thr Leu
145                 150                 155                 160

Tyr Gln Lys Ala Met Arg Leu Pro Leu Ser Leu Pro Val Gly Pro Arg
                165                 170                 175

Ile Pro Ala Ser Glu Leu Gln Pro Pro Ile Trp Asn Val Phe Ala Glu
            180                 185                 190

Ala Pro Ser Ala Val Leu Asn Asn Leu Lys Ala Arg Cys Ser Val Ser
            195                 200                 205

His Asn Lys Ile Thr Thr Phe Asn Gly Val Lys Phe Asn Tyr Ser Met
    210                 215                 220

Pro Gly Asn Cys Tyr His Ile Leu Ala Gln Asp Cys Ser Ser Glu Leu
225                 230                 235                 240

Lys Phe Leu Val Thr Met Lys Asn Ala Asp Glu Thr Thr Asn Leu Lys
                245                 250                 255

Ala Ile Asn Ile Lys Ile Gly Ser His Glu Ile Asp Met His Pro Val
                260                 265                 270

Asn Gly Gln Val Lys Leu Leu Val Asp Gly Ala Glu Ser Pro Thr Ala
            275                 280                 285

Asn Ile Ser Leu Val Ser Ala Gly Ala Ser Leu Trp Ile Arg Asn Glu
    290                 295                 300

Asn Gln Gly Leu Val Leu Val Gly Pro Ala Tyr Gly Ile Asp Thr Met
305                 310                 315                 320

Tyr Phe Asn Gly Gln Thr Phe Trp Ile Gln Val Pro Leu Trp Met Ala
                325                 330                 335

Gly Lys Thr Cys Gly Ile Cys Gly Lys Tyr Asp Ala Glu Tyr Lys Gln
                340                 345                 350

Glu Tyr Trp Met Pro Asn Gly Tyr Leu Ala Lys Asp Cys Val Ser Phe
            355                 360                 365

Gly His Ser Trp Ile Leu Glu Glu Thr Pro Cys Arg Gly Ala Cys Lys
    370                 375                 380

Leu His Arg Ser Phe Val Lys Leu Glu Lys Thr Val Gln Leu Ala Gly
385                 390                 395                 400

Val Asp Ser Lys
```